US006967245B2

(12) United States Patent
Adams et al.

(10) Patent No.: US 6,967,245 B2
(45) Date of Patent: Nov. 22, 2005

(54) UCP5

(75) Inventors: Sean Adams, Belmont, CA (US); James Pan, Belmont, CA (US)

(73) Assignee: Genentech, Inc., S. San Francisco, CA (US)

( * ) Notice: Subject to any disclaimer, the term of this patent is extended or adjusted under 35 U.S.C. 154(b) by 300 days.

(21) Appl. No.: 10/270,861

(22) Filed: Oct. 15, 2002

(65) Prior Publication Data

US 2003/0077749 A1 Apr. 24, 2003

Related U.S. Application Data

(63) Continuation of application No. 09/433,622, filed on Nov. 2, 1999.
(60) Provisional application No. 60/143,886, filed on Jul. 15, 1999, provisional application No. 60/129,583, filed on Apr. 16, 1999, and provisional application No. 60/110,286, filed on Nov. 30, 1998.

(51) Int. Cl.[7] .................. C07H 21/04; C12P 21/06; C12N 1/20; C12N 15/00; C07K 1/00

(52) U.S. Cl. ................ 536/23.5; 536/23.1; 435/69.1; 435/320.1; 435/325; 435/455; 435/252.3; 530/350

(58) Field of Search ................... 536/23.1, 23.5; 530/350, 333; 435/69.1, 320, 325, 455, 252.3, 183, 320.1

(56) References Cited

U.S. PATENT DOCUMENTS

| 4,775,662 A | 10/1988 | Gleason et al. |
| 5,010,003 A | 4/1991 | Chang et al. |
| 5,407,810 A | 4/1995 | Builder et al. |
| 5,663,304 A | 9/1997 | Builder et al. |
| 5,702,902 A | 12/1997 | Tartaglia |
| 6,602,694 B1 | 8/2003 | Albrandt et al. |

FOREIGN PATENT DOCUMENTS

| EP | 0 307 247 | 3/1989 |
| WO | WO 98/45438 | 10/1998 |
| WO | WO 98/52958 | 11/1998 |

OTHER PUBLICATIONS

Sequence alignment result 11, SEQ ID No: 2, 1–987.*
Sequence alignment result 11, SEQ ID No: 2, 10–987.*
Sequence alignment result 2, SEA ID No; 1 against nucleic acid database.*
Sequence alignment result 6, SEQ ID No: 1 against nucleic acid database.*
Sanchis et al. The J. of Biol. Chem., vol. 273. No; 51, pp 34611–34615, Dec. 18, 1998.*
Albrandt et al., "Human Uncoupling Protein 4," Database: A_Geneseq_36, Accession No. Y78511, 2000.
Altschul et al., "Local Alignment Statistics," Methods in Enzymology, 1996, 266: 460–480.
Bolivar et al., "Construction and Characterization of New Cloning Vehicles. II. A Multipurpose Cloning System," Gene, 1977, 2: 95–113.
Boss et al., "The Uncoupling Proteins, a Review," European J of Endocrinology, 1998, 139(1): 1–9.
Boss et al., "Uncoupling Protein–3: a New Member of the Mitochondrial Carrier Family With Tissue–Specific Expression," FEBS Lett, 1997, 408(1): 39–42.
Bouilland et al., "Molecular Approach to Thermogenesis in Brown Adipose Tissue: cDNA Cloning of the Mitochondrial Uncoupling Protein," PNAS USA, 1985, 82(2): 445–448.
Cassard et al., "Human Uncoupling Protein Gene: Structure, Comparison with Rat Gene, and Assignment to the Long Arm of Chromosome 4," J of Cellular Biochem., 1990, 43(3): 255–264.
EMBL Database: EMHUM1:AF078544 (Accession No. AF078544) 1998.
EMBL Database: EMROD:AB011068 (Accession No. AB011068) 1998.
Fleury et al., "Uncoupling Protein–2: a Novel Gene Linked to Obesity and Hyperinsulinemia," Nature Genetics, 1997, 15(3): 269–272.
Gibson et al., "A Novel Method for Real Time Quantitative RT–PCR," Genome Research, 1996, 6(10): 995–1001.
Gimeno et al., Cloning and Characterization of an Uncoupling Protein Homolog: A Potential Molecular Mediator of Human Thermogenesis, Diabetes, 1997, 46(5): 900–906.
Gong et al., "Uncoupling Protein–3 is a Mediator of Thermogenesis Regulated by Thyroid Hormone, β3–Adrenergic Agonists, and Leptin," J of Bio. Chem., 1997, 272(39): 24129–24133.
Gura, "Uncoupling Proteins Provide New Clue to Obesity's Causes," Science, 1998, 280(5368): 1369–1370.
Heid et al., "Real Time Quantitative PCR." Genome Research, 1996, 6(10): 986–994.
Holmes et al., "Structure and Functional Expression of a Human Interleukin–8 Receptor," Science, 1991, 253(5025): 1278–1280.
Jacobsson et al., "Mitochondrial Uncoupling Protein from Mouse Brown Fat. Molecular Cloning, Genetic Mapping, and mRNA Expression," J of Bio. Chem., 1985, 260(30): 16250–16354.

(Continued)

Primary Examiner—Jon Weber
Assistant Examiner—Rita Mitra
(74) Attorney, Agent, or Firm—Gates & Cooper LLP

(57) ABSTRACT

The present invention is directed to novel polypeptides having homology to certain human uncoupling proteins ("UCPs") and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention, and methods for producing the polypeptides of the present invention.

17 Claims, 17 Drawing Sheets

OTHER PUBLICATIONS

King et al., "Phenylephrine, Endothelin, Prostaglandin $F_{2\alpha}$ and Leukemia Inhibitory Factor Induce Different Cardiac Hypertrophy Phenotypes In Vitro," Endocrine, 1998, 9(1): 45–55.

Klaus et al., "Physiology of Transgenic Mice with Brown Fat Ablation: Obesity is Due to Lowered Body Temperature," Am. J of Physiology, 1998, 274(2 pt. 2): R287–R293.

Komarsoulis et al., "Human Secreted Protein Sequence Encoded by Gene 29, SEQ ID No. 152," Database: A_Geneseq_36, Accession No: Y91479.

Mao et al., "UCP4, a Novel Brain–Specific Mitochondrial Protein That Reduces Membrane Potential in Mammalian Cells," FEBS Lett., 1999, 443(3): 326–330.

NCBI/GenBank EST; Locus AA015735 (computer printout).
NCBI/GenBank EST; Locus AA015832 (computer printout).
NCBI/GenBank EST; Locus AA021118 (computer printout).
NCBI/GenBank EST; Locus AA021119 (computer printout).
NCBI/GenBank EST; Locus AA054608 (computer printout).
NCBI/GenBank EST; Locus AA056945 (computer printout).
NCBI/GenBank EST; Locus AA057005 (computer printout).
NCBI/GenBank EST; Locus AA142931 (computer printout).
NCBI/GenBank EST; Locus AA401224 (computer printout).
NCBI/GenBank EST; Locus AA404241 (computer printout).
NCBI/GenBank EST; Locus AA910774 (computer printout).
NCBI/GenBank EST; Locus AI032869 (computer printout).
NCBI/GenBank EST; Locus AI039086 (computer printout).
NCBI/GenBank EST; Locus AI128486 (computer printout).
NCBI/GenBank EST; Locus AI131262 (computer printout).
NCBI/GenBank EST; Locus AI241428 (computer printout).
NCBI/GenBank EST; Locus N48177 (computer printout).
NCBI/GenBank EST; Locus N53324 (computer printout).
NCBI/GenBank EST; Locus R19440 (computer printout).
NCBI/GenBank EST; Locus R44688 (computer printout).

Nicholls et al., "Thermogenic Mechanisms in Brown Fat," Physiological Rev., 1984, 64(1): 1–64.

O'Reilley et al., Baculovirus Expression Vectors: A Laboratory Manual, 1994, Oxford University Press.

Ott, An introduction to Statistical Methods and Data Analysis, 1988, Boston: PWS–Kent Publishing Co.

Palou et al., "The Uncoupling Protein, Thermogenin," Int'l. J of Biochem. & Cell Bio., 1998, 30(1): 7–11.

Rupperr et al., "Cloning and Expression of Human $TAF_{II}$ 250: A TBP–Associated Factor Implicated in Cell–Cycle Regulation," Nature, 1993, 362: 175–179.

Sanchis et al., "BMCP1, a Novel Mitochondrial Carrier with High Expression in the Central Nervous System of Humans and Rodents, and Respiration Uncoupling Activity in Recombinant Yeast," J. of Bio. Chem., 1998, 273(51): 34611–34615.

Sanchis et al., "Brain Mitochondrial Carrier Protein–1 (BMCP1)," Swiss Prot_39, Accession No. O95258, 2000.

Sanchis et al., "Homo Sapiens Brain Mitochondrial Carrier Protein–1 (BMCP1)," Database, GenEmbl, Accession No. AF078544, 1999.

Solanes et al., "The Human Uncoupling Protein–3 Gene. Genomic Structure. Chromosomal, Localization, and Genetic Basis for Short and Long Form Transcripts," J of Bio. Chem., 1997, 272(41):25433–25436.

Sompayrac et al., "Efficient Infection of Monkey Cells with DNA of Simian Virus 40," PNAS USA, 1981, 78(12): 7575–7578.

Surwit et al., "Differential Effects of Fat and Sucrose on the Development of Obesity and Diabetes in C57BL/61 and A/1 Mice," Metabolism, 1995, 44(5): 645–651.

Thimmappaya et al., "Adenovirus VAI RNA is Required for Efficient Translation of Viral mRNAs at Late Times After Infection," Cell, 1982, 31(3 pt. 2): 543–551.

Vidal–Puig et al., "UCP3: An Uncoupling Protein Homologue Expressed Preferentially and Abundantly in Skeletal Muscle and Brown Adipose Tissue," Biochem. & Biophys. Research Communications, 1997, 235(1): 79–82.

Wolf, "A New Uncoupling Protein: A Potential Component of the Human Body Weight Regulation System," Nutrition Reviews, 1997, 55(5): 178–179.

Yu et al., "Uncoupling Protein (UCP) Homolog mRNA Abundance in Brain & Other Tissues is Modified by Nutrition & Ambient Temperature," Experimental Biology Meeting, 1999.

* cited by examiner

```
UCP1   1  ............................MGGLTASDVHPTLGVQLFSAPIA
UCP2   1  ............................MVGFKATDVPPTATVKFLGAGTA
UCP3   1  ....................................MAVKFLGAGTA
UCP4   1  ......................MSVPEEEERLLPLTQRWPRASKFLLSGCA
UCP5   1  MGIFPGIILIFLRVKFATAAVIVSGHQKSTTVSHEMSGLNWKPFVYGGLA
                                                          I

UCP1  24  ACLADVITFPLDTAKVRLQVQGECP.......TSSVIRYKGVLGTITAVV
UCP2  24  ACIADLITFPLDTAKVRLQIQGESQGPVR...ATVSAQYRGVMGTILTMV
UCP3  12  ACFADLVTFPLDTAKVRLQIQGENQ.AVQ...TARLVQYRGVLGTILTMV
UCP4  30  ATVAELATFPLOTKTRLQMQGEAALARLGDGARESAPYRGMVRTALGII
UCP5  51  SIVAEFGTFPVDLTKTRLQVQGQSIDAR.....FKEIKYRGMFHALFRIC

UCP1  67  KTEGRMKLYSGLPAGLQRQISSASLRIGLYDTVQEFLTAGKET.APSLGS
UCP2  71  RTEGPRSLYNGLVAGLQRQMSFASVRIGLYDSVKQFYTKGSE..HASIGS
UCP3  58  RTEGPCSPYNGLVAGLQRQMSFASIRIGLYDSVKQVYTPKGAD.NSSLTT
UCP4  80  EEEGFLKLWQGVTPAIYRHVVYSGGRMVTYEHLREVVFGKSEDEHYPLWK
UCP5  96  KEEGVLALYSGIAPALLRQASYGTIKIGIYQSLKRLFVERLE..DETLLI
                      II

UCP1 116  KILAGLTTGVAFIGQPTEVVKVRLQAQSHLHG..IKPRYTGTYNAYRI
UCP2 119  RLLAGSTTGIALAVAAQPTDVVKVRFQAQARAG...GGRRYQSTVNAYKT
UCP3 107  RILAGCTTGAMAVTCAQPTDVVKVRFQASIHLGPSRSDRKYSGTMDAYRT
UCP4 130  SVIGMMAGVIGQFLANPTDLVKVQMQMEGKRKLEGKPLBFRGVHHAFAK
UCP5 144  NMICGVVSGVISSTIANPTOVLKIRMQAQGSLFQG...SMIGSFIDIYQQ
                  III

UCP1 164  IATTEGLTGLWKGTPNLMRSVIINCTELVTYDLMKEAFVKNNILADDVP
UCP2 166  IAREEGFRGLWKGTSPNVARNAIVNCAELVTYDLIKDALLKANLMTDDLP
UCP3 157  IAREEGVRGLWKGTLPNIMRNAIVNCAEVVTYDILKEKLLDYHLLTDNFP
UCP4 180  ILAEGGIRGLWAGWVPNIQRAALVNMGDLTTYDTVKHYLVLNTPLEDNIM
UCP5 191  EG....TRGLWRGVVPTAQRAAIVGVELPVYDITKKHLIILSGMMGDTIL
                                  IV

UCP1 214  CHLVSALIAGFCATAMSSPVDVVKTRFINSPPGQ.....YKSVPNCAMK
UCP2 215  CHFTSAFGAGFCTTVIASPVDVVKTRYMNSALGQ.....YSSAGHCALT
UCP3 207  CHFVSAFGAGFCATVVASPVDVVKTRYMNSPPGQ.....YFSPLDCMIK
UCP4 230  THGLSSLCSGLVASILGTPADVIKSRIMNQPRDKQGRGLLYKSSTDCLIQ
UCP5 237  THFVSSFTCGLAGALASNPVDVVRTRMMNQRAIVG-HVDLYKGTVDGILK
                V

UCP1 258  VFTNEGPTAFFKGLVPSFLRLGSWNVIMFVCFEQLKRELSKSRQTMDCAT
UCP2 260  MLQKEGPRAFYKGFMPSFLRLGSWNVVMFVTYEQLKRALMAACTSREAPF
UCP3 251  MVAQEGPTAFYKGFTPSFLRLGSWNVVMFVTYEQLKRALMKVQMLRESPF
UCP4 280  AVQGEGFMSLYKGFLPSWLRMTPWSMVFWLTYEKIREMSGVSPF......
UCP5 235  MWKHEGFFALYKGFWPNWLRLGPWNIIFEITYEQLKRLQI..........
                          VI
```

FIG._3A  FIG._3B  FIG._3C  FIG._3D

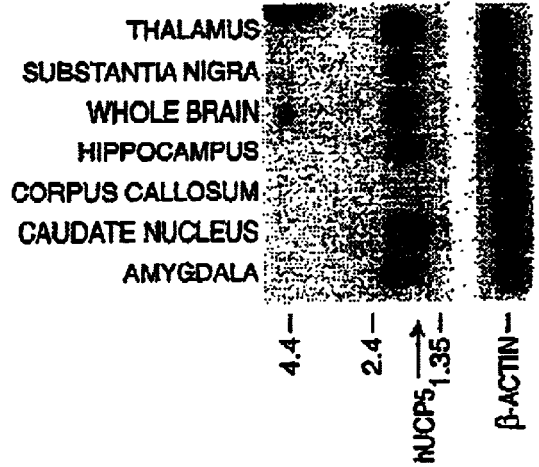
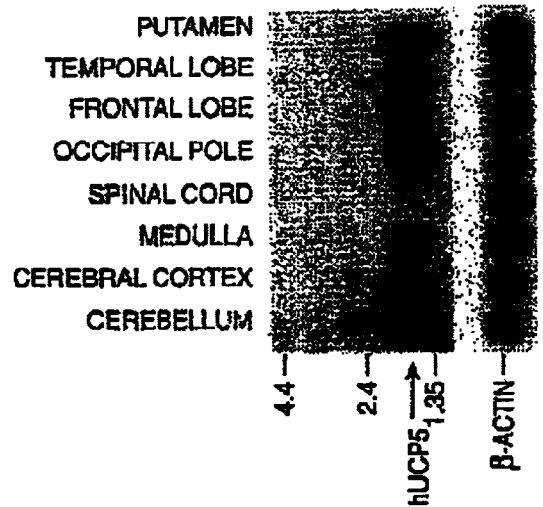
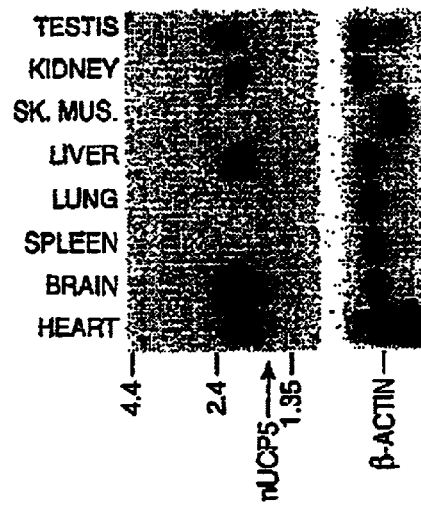

Fig. 3H

| Tissue | Total UCP5 mRNA (Fold- vs. Liver) | UCP5 LONG FORM (hUCP5L) % of Total UCP5 | UCP5 SHORT FORM (hUCP5S) % of Total UCP5* |
|---|---|---|---|
| Liver | 1.0 | 15% | 85% |
| Brain | 6.7 | 100% | n.d. |
| Heart | 2.1 | 31% | 69% |
| Kidney | 3.5 | 12% | 88% |
| Lung | 1.6 | 27% | 73% |
| Skeletal Muscle | 0.6 | 50% | 50% |
| Spleen | 1.3 | 21% | 79% |
| Stomach | 1.1 | 20% | 80% |
| Testis | 5.1 | 24% | 76% |
| Uterus | 2.6 | 21% | 79% |

*Relative abundance of UCP5S isoform mRNA was calculated as the difference between total UCP5 minus UCP5L mRNA. TaqMan primers/probes specifically recognizing either total or long-form UCP5 were employed for these analyses (Note: UCP5I was not detected in any sample).

n.d. = not detectable; below the threshold for accurate quantitiation

Fig. 3 I

| Tissue | Total UCP5 mRNA (Fold- vs. Liver) | UCP5 LONG FORM (mUCP5L) % of Total UCP5 | UCP5 SHORT FORM (mUCP5S) % of Total UCP5* |
|---|---|---|---|
| Liver | 1.0 | n.d. | 100% |
| Brown Adipose Tissue | 3.1 | n.d. | 100% |
| Brain | 46.2 | 2% | 98% |
| Heart | 0.5 | n.d. | 100% |
| Kidney | 3.4 | n.d. | 100% |
| Skeletal Muscle | 1.4 | n.d. | 100% |
| Spleen | 4.2 | n.d. | 100% |
| Testis | 16.4 | n.d. | 100% |
| White Adipose Tissue | 5.2 | 0.1% | 99.9% |

*Relative abundance of UCP5S isoform mRNA was calculated as the difference between total UCP5 minus UCP5L mRNA. TaqMan primers/probes specifically recognizing either total or long-form UCP5 were employed for these analyses (Note: UCP5SI was not detected in any sample).

n.d. = not detectable; below the threshold for accurate quantitation

FIGURE 5

```
ATGGGTATCTTTCCCGGAATAATCCTAATTTTTCTAAGGGTGAAGTTTGCAACGGCGGCC
GTGATTGTAAGCGGACACCAGAAAAGTACCACTGTAAGTCATGAGATGTCTGGTCTGAAT
TGGAAACCCTTTGTATATGGCGGCCTTGCCTCTATCGTGGCTGAGTTTGGGACTTTCCCT
GTGGACCTTACCAAAACACGACTTCAGGTTCAAGGCCAAAGCATTGATGCCCGTTTCAAA
GAGATAAAATATAGAGGGATGTTCCATGCGCTGTTTCGCATCTGTAAAGAGGAAGGTGTA
TTGGCTCTCTATTCAGGAATTGCTCCTGCGTTGCTAAGACAAGCATCATATGGCACCATT
AAAATTGGGATTTACCAAAGCTTGAAGCGCTTATTCGTAGAACGTTTAGAAGATGAAACT
CTTTTAATTAATATGATCTGTGGGGTAGTGTCAGGAGTGATATCTTCCACTATAGCCAAT
CCCACCGATGTTCTAAAGATTCGAATGCAGGCTCAAGGAAGCTTGTTCCAAGGGAGCATG
ATTGGAAGCTTTATCGATATATACCAACAAGAAGGCACCAGGGGTCTGTGGAGGGGTGTG
GTTCCAACTGCTCAGCGTGCTGCCATCGTTGTAGGAGTAGAGCTACCAGTCTATGATATT
ACTAAGAAGCATTTAATATTGTCAGGAATGATGGGCGATACAATTTTAACTCACTTCGTT
TCCAGCTTTACATGTGGTTTGGCTGGGGCTCTGGCCTCCAACCCGGTTGATGTGGTTCGA
ACTCGCATGATGAACCAGAGGGCAATCGTGGGACATGTGGATCTCTATAAGGGCACTGTT
GATGGTATTTTAAAGATGTGGAAACATGAGGGCTTTTTTGCACTCTATAAAGGATTTTGG
CCAAACTGGCTTCGGCTTGGACCCTGGAACATCATTTTTTTTATTACATACGAGCAGCTA
AAGAGGCTTCAAATCTAA
```

FIGURE 7
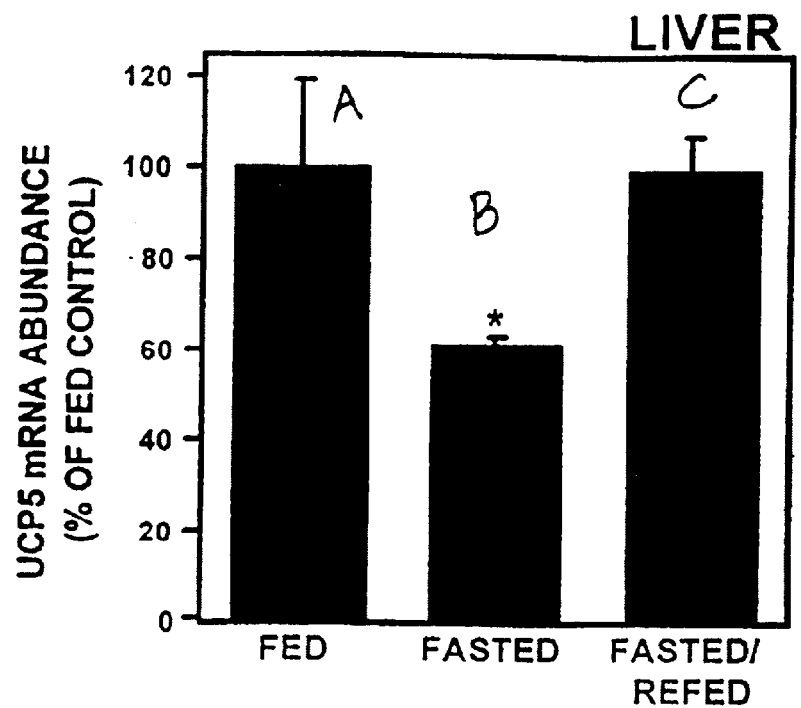
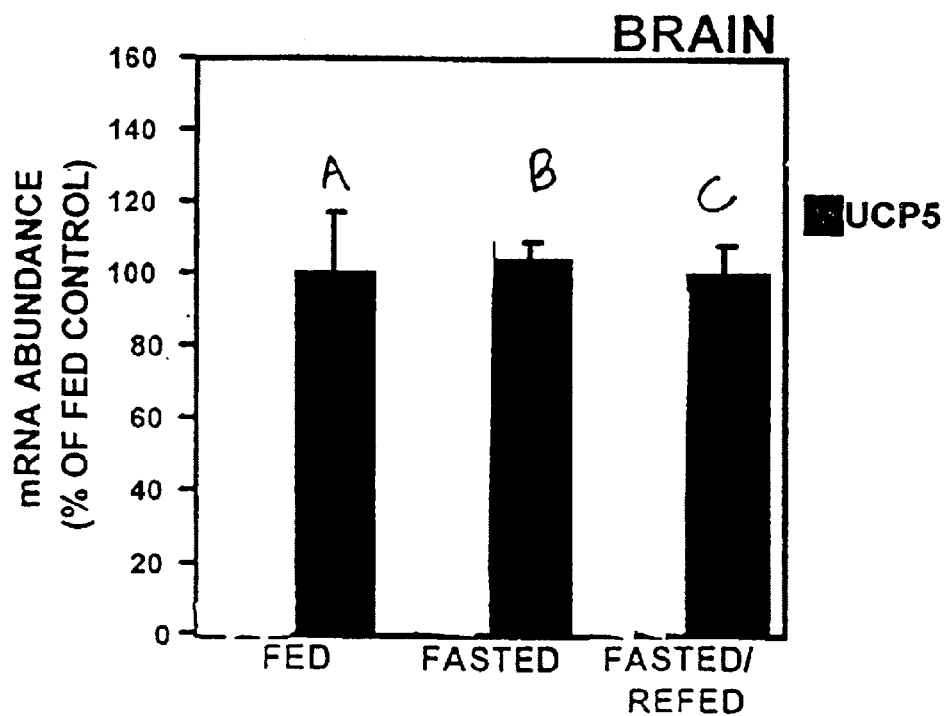
FIGURE 6

FIGURE 11
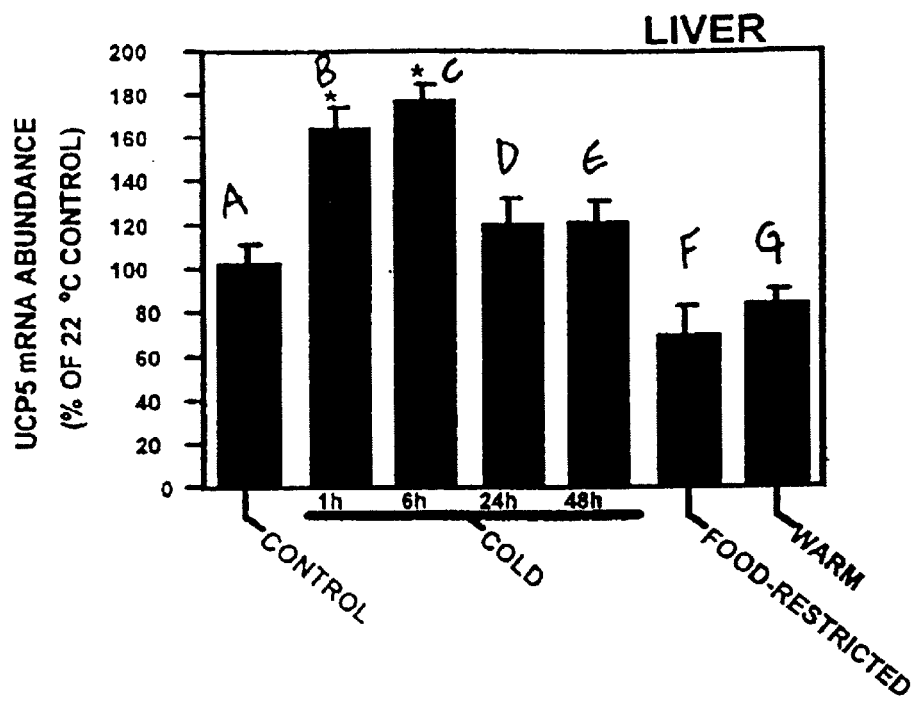
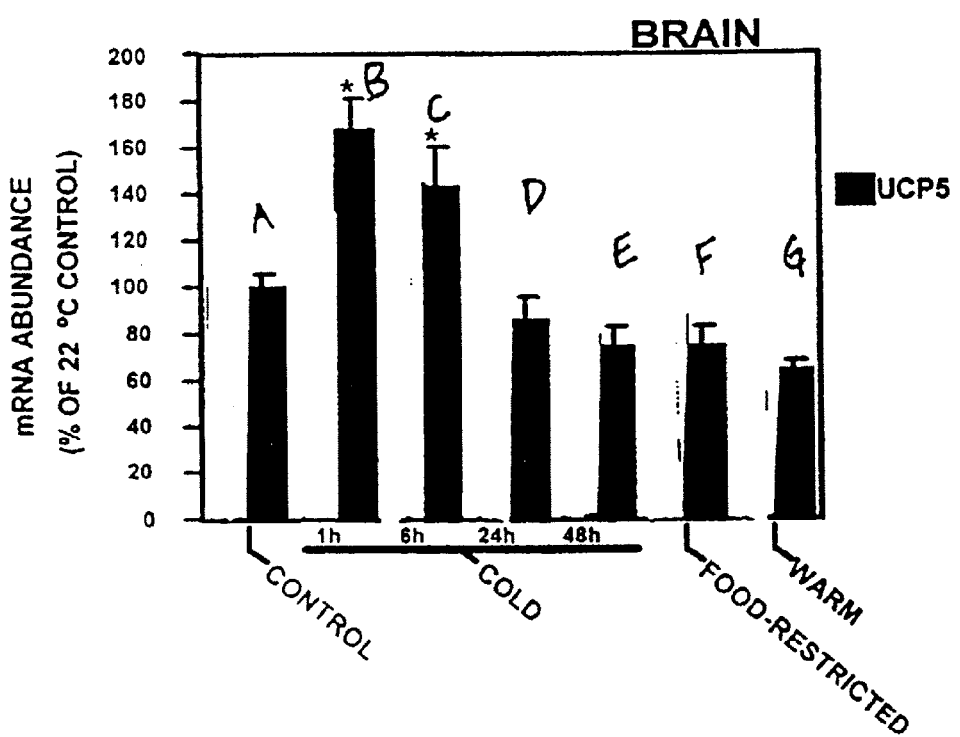
FIGURE 10

FIGURE 12 hUCP5S:
ATGGGTATCTTTCCCGGAATAATCCTAATTTTTCTAAGGGTGAAGTTTGCAACGGCGGCCGTGATTCACCAG
AAAAGTACCACTGTAAGTCATGAGATGTCTGGTCTGAATTGGAAACCCTTTGTATATGGCGGCCTTGCCTCTA
TCGTGGCTGAGTTTGGGACTTTCCCTGTGGACCTTACCAAAACACGACTTCAGGTTCAAGGCCAAAGCATTGA
TGCCCGTTTCAAAGAGATAAAATATAGAGGGATGTTCCATGCGCTGTTTCGCATCTGTAAAGAGGAAGGTGTA
TTGGCTCTCTATTCAGGAATTGCTCCTGCGTTGCTAAGACAAGCATCATATGGCACCATTAAAATTGGGATTT
ACCAAAGCTTGAAGCGCTTATTCGTAGAACGTTTAGAAGATGAAACTCTTTTAATTAATATGATCTGTGGGGT
AGTGTCAGGAGTGATATCTTCCACTATAGCCAATCCCACCGATGTTCTAAAGATTCGAATGCAGGCTCAAGGA
AGCTTGTTCCAAGGGAGCATGATTGGAAGCTTTATCGATATATACCAACAAGAAGGCACCAGGGGTCTGTGGA
GGGGTGTGGTTCCAACTGCTCAGCGTGCTGCCATCGTTGTAGGAGTAGAGCTACCAGTCTATGATATTACTAA
GAAGCATTTAATATTGTCAGGAATGATGGGCGATACAATTTTAACTCACTTCGTTTCCAGCTTTACATGTGGT
TTGGCTGGGGCTCTGGCCTCCAACCCGGTTGATGTGGTTCGAACTCGCATGATGAACCAGAGGGCAATCGTGG
GACATGTGGATCTCTATAAGGGCACTGTTGATGGTATTTTAAAGATGTGGAAACATGAGGGCTTTTTTGCACT
CTATAAAGGATTTTGGCCAAACTGGCTTCGGCTTGGACCCTGGAACATCATTTTTTTATTACATACGAGCAG
CTAAAGAGGCTTCAAATCTAAGAATTCAATCGATGGCCGCCATGGCCCAACTTGTTTATTG

Figure 13 hUCP5SI:
ATGGGTATCTTTCCCGGAATAATCCTAATTTTTCTAAGGGTGAAGTTTGCAACGGCGGCCGTGATTCACCAG
AAAAGTACCACTGTAAGTCATGAGATGTCTGGTCTGAATTGGAAACCCTTTGTATATGGCGGCCTTGCCTCTA
TCGTGGCTGAGTTTGGGACTTTCCCTGTGGACCTTACCAAAACACGACTTCAGGTTCAAGGCCAAAGCATTGA
TGCCCGTTTCAAAGAGATAAAATATAGAGGGATGTTCCATGCGCTGTTTCGCATCTGTAAAGAGGAAGGTGTA
TTGGCTCTCTATTCAGGAATTGCTCCTGCGTTGCTAAGACAAGCATCATATGGCACCATTAAAATTGGGATTT
ACCAAAGCTTGAAGCGCTTATTCGTAGAACGTTTAGAAGATGAAACTCTTTTAATTAATATGATCTGTGGGGT
AGTGTCAGGAGTGATATCTTCCACTATAGCCAATCCCACCGATGTTCTAAAGATTCGAATGCAGGCTCAAGGA
AGCTTGTTCCAAGGGAGCATGATTGGAAGCTTTATCGATATATACCAACAAGAAGGCACCAGGGGTCTGTGGA
GGTGCTTATGTTCAAAAGCTGTTACCGGCTGTGTGCTGTGGCTCATGCCTGTAATCCCAGCACTTTGGGAGGC
CAACGCGGGTGGATCACTTGAGGGTGTGGTTCCAACTGCTCAGCGTGCTGCCATCGTTGTAGGAGTAGAGCTA
CCAGTCTATGATATTACTAAGAAGCATTTAATATTGTCAGGAATGATGGGCGATACAATTTTAACTCACTTCG
TTTCCAGCTTTACATGTGGTTTGGCTGGGGCTCTGGCCTCCAACCCGGTTGATGTGGTTCGAACTCGCATGAT
GAACCAGAGGGCAATCGTGGGACATGTGGATCTCTATAAGGGCACTGTTGATGGTATTTTAAAGATGTGGAAA
CATGAGGGCTTTTTTGCACTCTATAAAGGATTTTGGCCAAACTGGCTTCGGCTTGGACCCTGGAACATCATTT
TTTTTATTACATACGAGCAGCTAAAGAGGCTTCAAATCTAAGAATTCAATCGATGGCCGCCATGGCCCAACTT
GTTATAATG

Figure 14 mUCP5S:
CTGCAGGTCGACTCTAGAGGATCCGAAATGGGTATCTTTCCCGGAATAATCCTAATTTTTCTAAGGGTGAAG
TTTGCAACGGCGGCAGTGATTCATCAGAAAAGTTCCACTTTAAGCCATGAGATGTCTGGTCTGAACTGGAAAC
CTTTTGTGTATGGCGGCCTTGCCTCTATTGTTGCCGAGTTCGGCACTTTCCCTGTGGATCTTACTAAAACACG
GCTGCAAGTCCAAGGCCAGAGTATCGATGTTCGTTTCAAAGAAATAAAATATAGAGGGATGTTTCATGCCTTG
TTCCGAATCTATAAAGAAGAAGGGATCTTGGCTCTGTATTCAGGAATTGCCCCTGCGTTACTAAGACAGGCAT
CATATGGCACCATCAAAATTGGTATTTATCAAAGCTTGAAGCGATTATTTGTAGAACGTTTGGAAGATGAGAC
TCTCCTAATTAACATGATCTGTGGGGTAGTGTCAGGAGTGATTTCCTCTACTATTGCCAATCCCACTGATGTT
CTAAAGATTCGAATGCAGGCTCAAGGAAGTTTGTTCCAAGGGAGCATGATTGGCAGCTTCATTGACATATACC
AGCAAGAAGGTACCAGGGGTCTGTGAGGGGTGTGGTCCCAACTGCTCAGCGTGCTGCAATCGTTGTGGGAGT
AGAGCTGCCCGTTTATGATATTACCAAGAAGCACCTGATAGTTTCAGGAATGCTGGGAGACACAATTTTAACA
CACTTTGTTTCCAGTTTCACCTGTGGTTTGGCTGGGGCTCTGGCATCTAACCCTGTGGATGTGGTGAGAACTC
GAATGATGAATCAGAGGGCAATAGTGGGACATGTGGACCTCTACAAGGGTACTTTGGATGGTATTTTAAAGAT
GTGGAAGCATGAGGGATTTTTTGCACTCTATAAAGGATTTTGGCCAAACTGGCTTCGACTTGGACCCTGGAAC
ATCATTTTTTTTATTACCTATGAGCAGCTCAAGAGGCTTCAGATCTAAGAATTCAATCGATGGCCGCCATGGC
C

Figure 15 mUCP5L:
CTGCAGGTCGACTCTAGAGGATCCGAAATGGGTATCTTTCCCGGAATAATCCTAATTTTTCTAAGGGTGAAG
TTTGCAACGGCGGCAGTGATTGTAAGCGGACATCAGAAAAGTTCCACTTTAAGCCATGAGATGTCTGGTCTGA
ACTGGAAACCTTTTGTGTATGGCGGCCTTGCCTCTATTGTTGCCGAGTTCGGCACTTTCCCTGTGGATCTTAC
TAAAACACGGCTGCAAGTCCAAGGCCAGAGTATCGATGTTCGTTTCAAAGAAATAAAATATAGAGGGATGTTT
CATGCCTTGTTCCGAATCTATAAAGAAGAAGGGATCTTGGCTCTGTATTCAGGAATTGCCCCTGCGTTACTAA
GACAGGCATCATATGGCACCATCAAAATTGGTATTTATGAAAGCTTGAAGCGATTATTTGTAGAACGTTTGGA
AGATGAGACTCTCCTAATTAACATGATCTGTGGGGTAGTGTCAGGAGTGATTTCCTCTACTATTGCCAATCCC
ACTGATGTTCTAAAGATTCGAATGCAGGCTCAAGGAAGTTTGTTCCAAGGGAGCATGATTGGCAGCTTCATTG
ACATATACCAGCAAGAAGGTACCAGGGGTCTGTGGAGGGGTGTGGTCCCAACTGCTCAGCGTGCTGCAATCGT
TGTGGGAGTAGAGCTGCCCGTTTATGATATTACCAAGAAGCACCTGATAGTTTCAGGAATGCTGGGAGACACA
ATTTTAACACACTTTGTTTCCAGTTTCACCTGTGGTTTGGCTGGGGCTCTGGCATCTAACCCTGTGGATGTGG
TGAGAACTCGAATGATGAATCAGAGGGCAATAGTGGGACATGTGGACCTCTACAAGGGTACTTTGGATGGTAT
TTTAAAGATGTGGAAGCATGAGGGATTTTTTGCACTCTATAAAGGATTTTGGCCAAACTGGCTTCGACTTGGA
CCCTGGAACATCATTTTTTTATTACCTATGAGCAGCTCAAGAGGCTTCAGATCTAAGAATTCAATCGATGGC
CGCCATGGCC

Figure 16

```
  1 MGIFPGIILIFLRVKFATAAVI VSG HQKSTTVSHEMSGLNWKPFV  hUCP5L
  1 MGIFPGIILIFLRVKFATAAVI --- HQKSTTVSHEMSGLNWKPFV  hUCP5S
  1 MGIFPGIILIFLRVKFATAAVI --- HQKSTTVSHEMSGLNWKPFV  hUCP5SI
  1 MGIFPGIILIFLRVKFATAAVI VSG HQKSSTLSHEMSGLNWKPFV  mUCP5L
  1 MGIFPGIILIFLRVKFATAAVI ::: HQKSSTLSHEMSGLNWKPFV  mUCP5S

46 YGGLASIVAEFGTFPVDLTKTRLQVQGQSIDARFKEIKYRGMFHA  hUCP5L
 43 YGGLASIVAEFGTFPVDLTKTRLQVQG-QSIDARFKEIKYRGMFHA  hUCP5S
 43 YGGLASIVAEFGTFPVDLTKTRLQVQGQSIDARFKEIKYRGMFHA  hUCP5SI
 46 YGGLASIVAEFGTFPVDLTKTRLQVQGQSIDVRFKEIKYRGMFHA  mUCP5L
 43 YGGLASIVAEFGTFPVDLTKTRLQVQGQSIDVRFKEIKYRGMFHA  mUCP5S
                    I

91 LFRICKEEGVLALYSGIAPALLRQASYGTIKIGIYQSLKRLFVER  hUCP5L
 88 LFRICKEEGVLALYSGIAPALLRQASYGTIKIGIYQSLKRLFVER  hUCP5S
 88 LFRICKEEGVLALYSGIAPALLRQASYGTIKIGIYQSLKRLFVER  hUCP5SI
 91 LFRIYKEEGILALYSGIAPALLRQASYGTIKIGIYQSLKRLFVER  mUCP5L
 88 LFRIYKEEGILALYSGIAPALLRQASYGTIKIGIYQSLKRLFVER  mUCP5S
                    II

136 LEDETLLINMICGVVSGYISSTIANPTDVLKIRMQAQGSLFQGSM  hUCP5L
133 LEDETLLINMICGVVSGYISSTIANPTDVLKIRMQAQGSLFQGSM  hUCP5S
133 LEDETLLINMICGVVSGYISSTIANPTDVLKIRMQAQGSLFQGSM  hUCP5SI
136 LEDETLLINMICGVVSGYISSTIANPTDVLKIRMQAQGSLFQGSM  mUCP5L
133 LEDETLLINMICGVVSGYISSTIANPTDVLKIRMQAQGSLFQGSM  mUCP5S
                    III

181 IGSFIDIYQQEGTRGLWR-------------------------  hUCP5L
178 IGSFIDIYQQEGTRGLWR-------------------------  hUCP5S
178 IGSFIDIYQQEGTRGLWR CLCSKAVTGCVLWLMPVIPALWEANAG  hUCP5SI
181 IGSFIDIYQQEGTRGLWR-------------------------  mUCP5L
178 IGSFIDIYQQEGTRGLWR-------------------------  mUCP5S

199 ----GVVPTAQRAAIVVGVELPVYDITKKHLILSGMMGDTILTHF  hUCP5L
196 ----GVVPTAQRAAIVVGVELPVYDITKKHLILSGMMGDTILTHF  hUCP5S
223 GSLEGVVPTAQRAAIVVGVELPVYDITKKHLILSGMMGDTILTHF  hUCP5SI
199 ----GVVPTAQRAAIVVGVELPVYDITKKHLIVSGMLGDTILTHF  mUCP5L
196 ----GVVPTAQRAAIVVGVELPVYDITKKHLIVSGMLGDTILTHF  mUCP5S
                    IV

248 VSSFTCGLAGALASNPVDVVRTRMMNQRAIVGHVDLYKGTVDGIL  hUCP5L
237 VSSFTCGLAGALASNPVDVVRTRMMNQRAIVGHVDLYKGTVDGIL  hUCP5S
268 VSSFTCGLAGALASNPVDVVRTRMMNQRAIVGHVDLYKGTVDGIL  hUCP5SI
240 VSSFTCGLAGALASNPVDVVRTRMMNQRAIVGHVDLYKGTLDGIL  mUCP5L
237 VSSFTCGLAGALASNPVDVVRTRMMNQRAIVGHVDLYKGTLDGIL  mUCP5S
                    V

285 KMWKHEGFFALYKGFWPNWLRLGPWNIIFFITYEQLKRLQI  hUCP5L
282 KMWKHEGFFALYKGFWPNWLRLGPWNIIFFITYEQLKRLQI  hUCP5S
313 KMWKHEGFFALYKGFWPNWLRLGPWNIIFFITYEQLKRLQI  hUCP5SI
285 KMWKHEGFFALYKGFWPNWLRLGPWNIIFFITYEQLKRLQI  mUCP5L
282 KMWKHEGFFALYKGFWPNWLRLGPWNIIFFITYEQLKRLQI  mUCP5S
                    VI
```

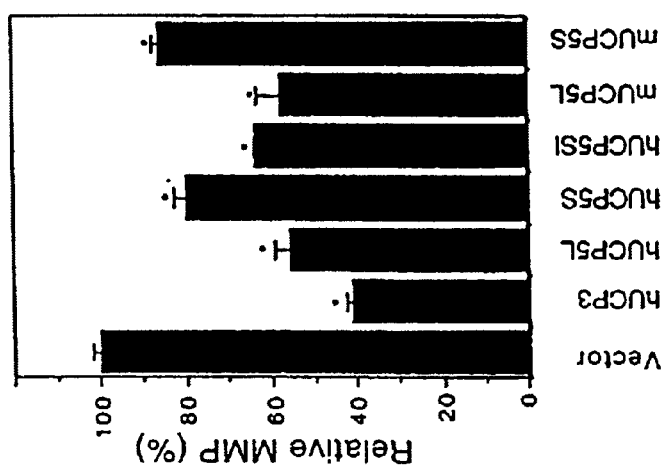
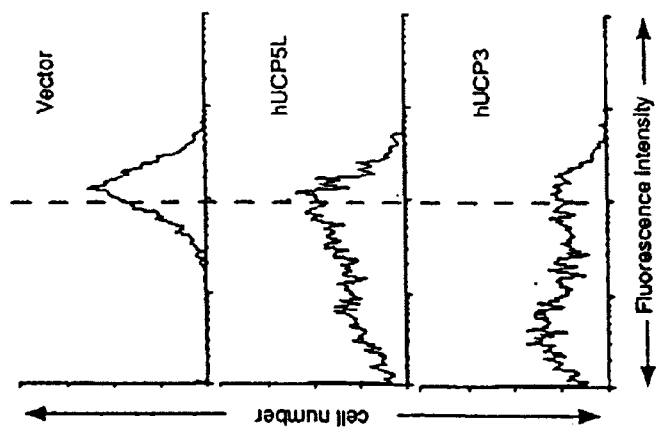
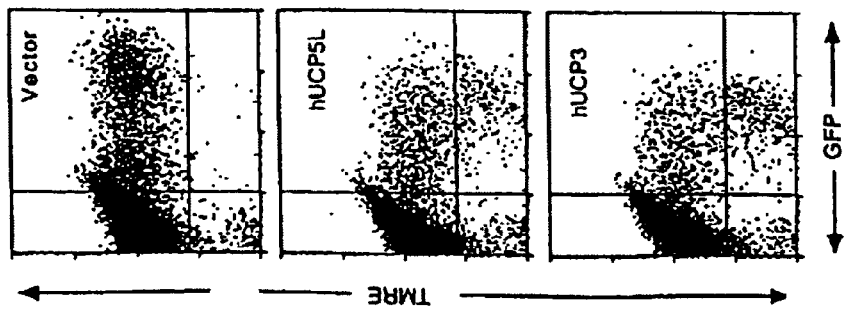
Fig. 17

UCP5

RELATED APPLICATIONS

This application is a continuation application of U.S. patent application Ser. 09/433,622 filed Nov. 2, 1999, nonprovisional application filed under 37 CFR 1.53(b) claiming priority under section 119 to provisional application No. 60/110,286 filed Nov. 30, 1998, Ser. No. 60/129,583 filed Apr. 16, 1999, and Ser. No. 60/143,886 filed Jul. 15, 1999, the contents of which are incorporated herein by reference.

FIELD OF THE INVENTION

The present invention relates generally to the identification and isolation of novel DNA having homology to certain human uncoupling proteins, and to the recombinant production of novel polypeptides, designated herein as "uncoupling protein 5" or "UCP5."

BACKGROUND OF THE INVENTION

Uncoupling proteins or "UCPs", believed to play a role in the metabolic process, have been reported in the literature. UCPs were first found and described in the brown fat cells of hibernating animals, such as bears. UCPs were believed to help such hibernators and other cold-weather adapted animals maintain core body temperatures in cold weather by raising their body's resting metabolic rate. Because humans possess relatively small quantities of brown adipose tissue, UCPs were originally thought to play a minor role in human metabolism.

Several different human uncoupling proteins have now been described. [See, generally, Gura, *Science*, 280:1369–1370 (1998)]. The human uncoupling protein referred to as UCP1 was identified by Nicholls et al. Nicholls et al. showed that the inner membrane of brown fat cell mitochondria was very permeable to proteins, and the investigators traced the observed permeability to a protein, called UCP1, in the mitochondrial membrane. Nicholls et al. reported that the UCP1, by creating such permeability, reduced the number of ATPs that can be made from a food source, thus raising body metabolic rate and generating heat. [Nicholls et al., *Physiol. Rev.*, 64, 1–64 (1984)].

It was later found that UCP1 is indeed expressed only in brown adipose tissue [Bouillaud et al., *Proc. Natl. Acad. Sci.*, 82:445–448 (1985); Jacobsson et al., *J. Biol. Chem.*, 260:16250–16254 (1985)]. Genetic mapping studies have shown that the human UCP1 gene is located on chromosome 4. [Cassard et al., *J. Cell. Biochem.*, 43:255–264 (1990)]. UCP1 recently has been called thermogenin. [Palou et al., *Int. J. Biochem. & Cell Bio.*, 30: 7–11 (1998)]. Palou et al. describe that UCP1 synthesis and activity are regulated by norepinephrine. [Palou et al., supra].

Another human UCP, referred to as C5 or UCPH or UCP2, has also been described. [Gimeno et al., *Diabetes*, 46:900–906 (1997); Fleury et al., *Nat. Genet.*, 15:269–272 (1997); Boss et al., *FEBS Letters*, 408:39–42 (1997); see also, Wolf, *Nutr. Rev.*, 55:178–179 (1997); U.S. Pat. No. 5,702,902]. Fleury et al. teach that the UCP2 protein has 59% amino acid identity to UCP1, and that UCP2 maps to regions of human chromosome 11 which have been linked to hyperinsulinaemia and obesity. [Fleury et al., supra]. It has also been reported that UCP2 is expressed in a variety of adult tissues, such as brain and muscle and fat cells. [Gimeno et al., supra, and Fleury et al., supra]. Similarly, U.S. Pat. No. 5,702,902 reported a relatively complex pattern of tissue distribution, with mRNA accumulation appearing to be greatest in muscle tissue.

A third human UCP, UCP3, was recently described in Boss et al., supra; Vidal-Puig et al., *Biochem. Biophys. Res. Comm.*, 235:79–82 (1997); Solanes et al., *J. Biol. Chem.*, 272:25433–25436 (1997); and Gong et al., *J. Biol. Chem.*, 272:24129–24132 (1997). [See also Great Britain Patent No. 9716886]. Solanes et al. report that unlike UCP1 and UCP2, UCP3 is expressed preferentially in human skeletal muscle, and that the UCP3 gene maps to human chromosome 11, adjacent to the UCP2 gene. [Solanes et al., supra]. Gong et al. describe that the UCP3 expression can be regulated by known thermogenic stimuli, such as thyroid hormone, beta3-andrenergic agonists and leptin. [Gong et al., supra].

UCP1, UCP2, and UCP3 share several characteristics with mitochondrial membrane transporters. [Boss et al., *Euro. J. Endocrinology*, 139: 1–9 (1998)]. All three UCPs are about 300 amino acids long and have a molecular mass of about 30 kDa. [Boss et al., supra]. Each also has three typical mitochondrial energy transfer protein signatures. [Boss et al., supra].

SUMMARY OF THE INVENTION

A cDNA clone (DNA 80562-1663) has been identified, having certain homologies to some known human uncoupling proteins, that encodes a novel polypeptide, designated in the present application as "UCP5."

In one embodiment, the invention provides an isolated nucleic acid molecule comprising DNA encoding a UCP5 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a UCP5 polypeptide comprising the sequence of amino acid residues from about 1 to about 325, inclusive of FIG. 1 (SEQ ID NO: 1), or (b) the complement of the DNA molecule of (a).

In another aspect, the invention concerns an isolated nucleic acid molecule encoding a UCP5 polypeptide comprising DNA hybridizing to the complement of the nucleic acid between about nucleotides 10 and about 987 inclusive, of FIG. 1 (SEQ ID NO: 2). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203325, or (b) the complement of the DNA molecule of (a). In a preferred embodiment, the nucleic acid comprises a DNA encoding the same mature polypeptide encoded by the human protein cDNA in ATCC Deposit No. 203325.

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 1 to about 325, inclusive of FIG. 1 (SEQ ID NO: 1), or the complement of the DNA of (a).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 to about 325, inclusive of FIG. 1 (SEQ ID NO: 1), or (b) the complement of the DNA of (a).

Further embodiments of the invention are directed to fragments of the UCP5 coding sequence, which are sufficiently long to be used as hybridization probes. Preferably, such fragments contain at least about 20 to about 80 consecutive bases included in the sequence of FIG. 1 (SEQ ID NO: 2). Optionally, such fragments include the N-terminus or the C-terminus of the sequence of FIG. 1 (SEQ ID NO: 2).

In another embodiment, the invention provides a vector comprising DNA encoding UCP5 or its variants. The vector may comprise any of the isolated nucleic acid molecules hereinabove defined.

A host cell comprising such a vector is also provided. By way of example, the host cells may be CHO cells, *E. coli*, or yeast. A process for producing UCP5 polypeptides is further provided and comprises culturing host cells under conditions suitable for expression of UCP5 and recovering UCP5 from the cell culture.

In another embodiment, the invention provides isolated UCP5 polypeptide encoded by any of the isolated nucleic acid sequences hereinabove defined.

In a specific aspect, the invention provides isolated native sequence UCP5 polypeptide, which in one embodiment, includes an amino acid sequence comprising residues 1 to 325 or residues 20 to 325 of FIG. 1 (SEQ ID NO: 1).

In another aspect, the invention concerns an isolated UCP5 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 to 325 or residues 20 to 325, of FIG. 1 (SEQ ID NO: 1).

In a further aspect, the invention concerns an isolated UCP5 polypeptide, comprising an amino acid sequence scoring at least about 80% positives, preferably at least about 85% positives, more preferably at least about 90% positives, most preferably at least about 95% positives when compared with the amino acid sequence of residues 1 to 325 or residues 20 to 325 of FIG. 1 (SEQ ID NO: 1).

In yet another aspect, the invention concerns an isolated UCP5 polypeptide, comprising the sequence of amino acid residues 1 to about 325 or residues 20 to 325, of FIG. 1 (SEQ ID NO: 1), or a fragment thereof sufficient to, for instance, provide a binding site for an anti-UCP5 antibody. Preferably, the UCP5 fragment retains at least one biological activity of a native UCP5 polypeptide.

In a still further aspect, the invention provides a polypeptide produced by (i) hybridizing a test DNA molecule under stringent conditions with (a) a DNA molecule encoding a UCP5 polypeptide comprising the sequence of amino acid residues from about 1 to about 325 of FIG. 1 (SEQ ID NO: 1), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In another embodiment, the invention provides chimeric molecules comprising a UCP5 polypeptide fused to a heterologous polypeptide or amino acid sequence. An example of such a chimeric molecule comprises a UCP5 polypeptide fused to an epitope tag sequence or a Fc region of an immunoglobulin.

In another embodiment, the invention provides an antibody which specifically binds to UCP5 polypeptide. Optionally, the antibody is a monoclonal antibody.

In yet another embodiment, the invention concerns agonists and antagonists of the native UCP5 polypeptide. In a particular embodiment, the agonist or antagonist is an anti-UCP5 antibody.

In a further embodiment, the invention concerns a method of identifying agonists or antagonists of a native UCP5 polypeptide, by contacting the native UCP5 polypeptide with a candidate molecule and monitoring the desired activity. The invention also provides therapeutic methods and diagnostic methods using UCP5.

In a still further embodiment, the invention concerns a composition comprising a UCP5 polypeptide, or an agonist or antagonist as hereinabove defined, in combination with a carrier.

BRIEF DESCRIPTION OF THE DRAWINGS

FIG. 1 shows the nucleotide sequence of a cDNA encoding native sequence UCP5 (SEQ ID NO: 2), the complement of the nucleotide sequence of a cDNA encoding native sequence UCP5 (SEQ ID NO: 32), and the corresponding derived amino acid sequence of a native sequence UCP5 (SEQ ID NO: 1).

FIG. 2 shows an amino acid sequence alignment of UCP5 with other uncoupling proteins, UCP1 (SEQ ID NO: 33), UCP2 (SEQ ID NO: 34), UCP3 (SEQ ID NO: 35), UCP4 (SEQ ID NO: 36), and UCP5 (SEQ ID NO: 1). The six putative transmembrane domains are shown and are underlined (and labeled I to VI, respectively). The asterisks (*) shown below the protein sequence indicate three (3) putative mitochondrial carrier protein motifs. A putative nucleotide binding domain is double underlined.

FIGS. 3A–3G show the results of Northern blot analysis. Human adult tissues (A–C), cancer cell lines (D), human adult brain tissue (E, F) and mouse multiple tissues (G) (Clontech) were probed with human or mouse UCP5 cDNA.

FIGS. 3H–3I show the results of real time quantitative RT-PCR assays performed using primers and probes with specificities toward total UCP5, mUCP5L, or UCP5SI, and using RNA from various human (H) and murine (I) tissues.

FIG. 5 shows a "from DNA" sequence (SEQ ID NO: 5) assembled from selected EST sequences.

FIGS. 6A–6C show the results of in vitro assays conducted to determine the effect of food consumption on the expression of UCP5 mRNA in brain tissue.

FIGS. 7A–7C show the results of in vitro assays conducted to determine the effect of food consumption on the expression of UCP5 mRNA in liver tissue.

FIGS. 10A–10G show the results of in vitro assays conducted to determine the effect of temperature stress on the expression of UCP5 mRNA in brain tissue.

FIGS. 11A–11G show the results of in vitro assays conducted to determine the effect of temperature stress on the expression of UCP5 mRNA in liver tissue.

FIG. 12 shows the nucleotide sequence of a cDNA encoding hUCP5S (SEQ ID NO: 6).

FIG. 13 shows the nucleotide sequence of a cDNA encoding hUCP5SI (SEQ ID NO: 8).

FIG. 14 shows the nucleotide sequence of a cDNA encoding mUCP5S (SEQ ID NO: 10).

FIG. 15 shows the nucleotide sequence of a cDNA encoding mUCP5L (SEQ ID NO: 12).

FIG. 16 shows an amino acid sequence alignment of isoforms of UCP5, hUCP5L (SEQ ID NO: 1), hUCP5S (SEQ ID NO: 7), hUCP5SI (SEQ ID NO: 9), mUCP5L (SEQ ID NO: 13), and mUCP5S (SEQ ID NO: 11). The six putative transmembrane domains are shown and are underlined (and labeled I to VI, respectively). The asterisks (*) shown below the protein sequence indicates putative mitochondrial carrier protein motifs. A putative nucleotide binding domain is double underlined.

FIGS. 17A–17C show results of in vitro assays conducted to determine the effect of UCP5 expression on mitochondrial membrane potential.

DETAILED DESCRIPTION OF THE PREFERRED EMBODIMENTS

I. Definitions

Figure 4:
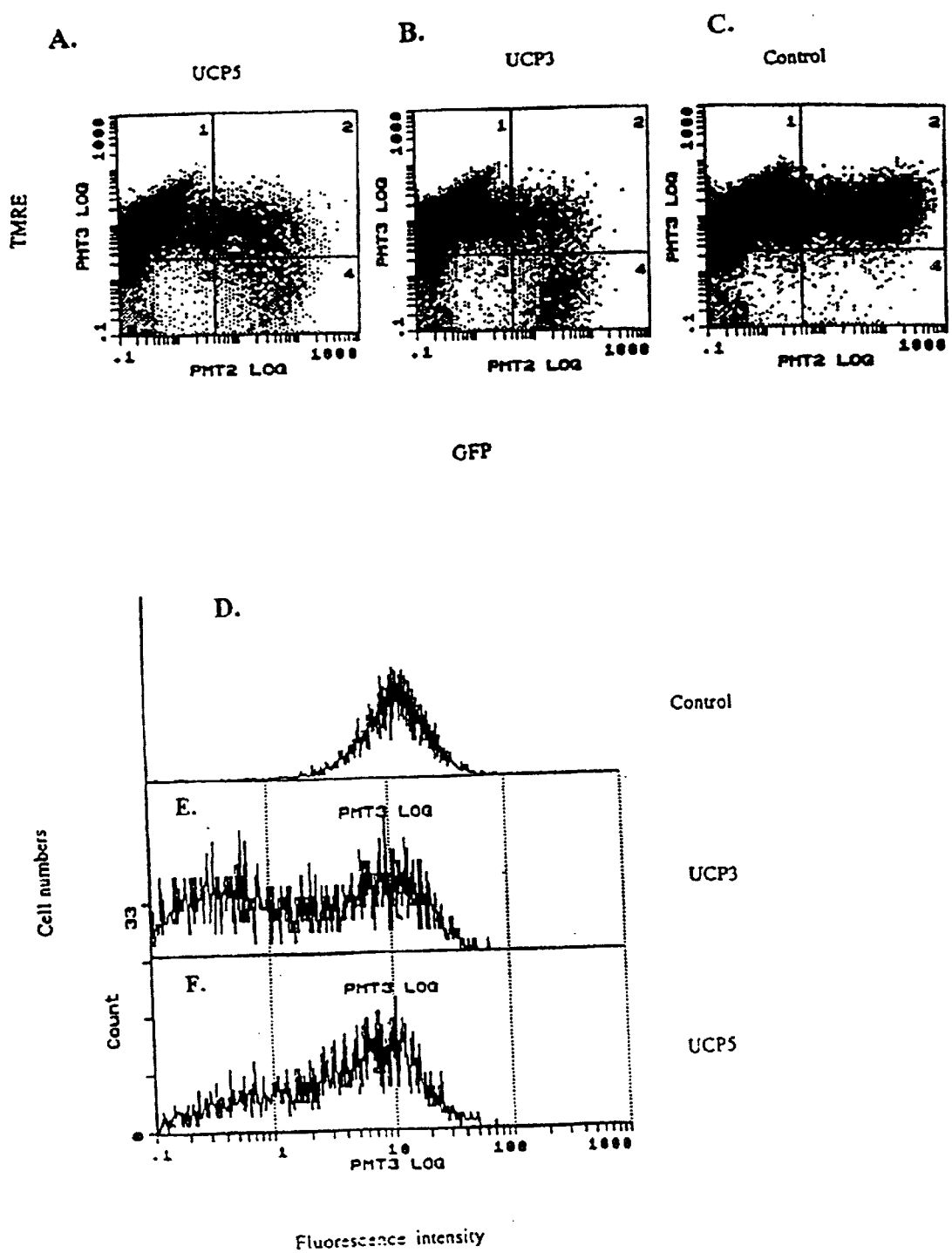
FIGS. 4A–4F show the results of in vitro assays conducted to determine the effects of UCP5 expression on mitochondrial membrane potential.

The terms "UCP5 polypeptide", "UCP5 protein" and "UCP5" when used herein encompass native sequence UCP5 and UCP5 variants (which are further defined herein). The UCP5 may be isolated from a variety of sources, such as from human tissue types or from another source, or prepared by recombinant and/or synthetic methods.

A "native sequence UCP5" comprises a polypeptide having the same amino acid sequence as a UCP5 derived from nature. Such native sequence UCP5 can be isolated from nature or can be produced by recombinant and/or synthetic means. The term "native sequence UCP5" specifically encompasses naturally-occurring truncated forms or isoforms, naturally-occurring variant forms (e.g., alternatively spliced forms) and naturally-occurring allelic variants of the UCP5. In one embodiment of the invention, the native sequence UCP5 is a mature or full-length human native sequence UCP5 ("hUCP5L") comprising amino acids 1 to 325 of FIG. 1 (SEQ ID NO: 1).

Figure 1:
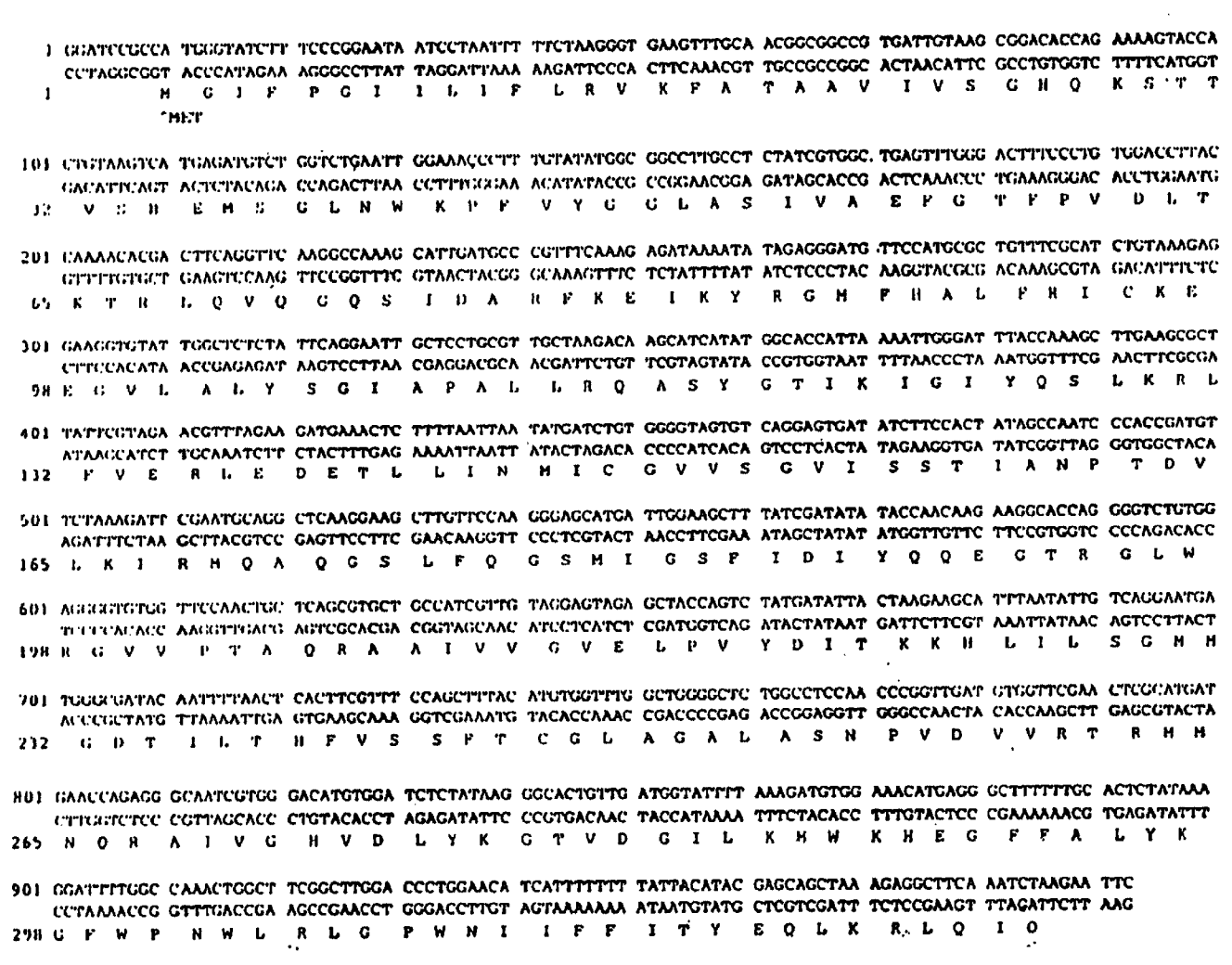

"UCP5 variant" means anything other than a native sequence UCP5, and includes UCP5 having at least about 80% amino acid sequence identity with the amino acid sequence of residues 1 to 325 of the UCP5 polypeptide having the deduced amino acid sequence shown in FIG. 1 (SEQ ID NO: 1). Such UCP5 variants include, for instance, UCP5 polypeptides wherein one or more amino acid residues are added, or deleted, at the N- or C-terminus, as well as within one or more internal domains, of the sequence of FIG. 1 (SEQ ID NO: 1). Ordinarily, a UCP5 variant will have at least about 80% amino acid sequence identity, more preferably at least about 85% amino acid sequence identity, even more preferably at least about 90% amino acid sequence identity, and most preferably at least about 95% amino acid sequence identity with the amino acid sequence of residues 1 to 325 of FIG. 1 (SEQ ID NO: 1).

The term "hUCP5S" as used herein refers to the polypeptide identified from human tissue comprising the amino acid sequence of FIG. 16 (SEQ ID NO: 7).

The term "hUCP5SI" as used herein refers to the polypeptide identified from human tissue comprising the amino acid sequence of FIG. 16 (SEQ ID NO: 9).

The term "mUCP5L" as used herein refers to the polypeptide identified from murine tissue comprising the amino acid sequence of FIG. 16 (SEQ ID NO: 13).

The term "mUCP5S" as used herein refers to the polypeptide identified from murine tissue comprising the amino acid sequence of FIG. 16 (SEQ ID NO: 11).

"Percent (%) amino acid sequence identity" with respect to the sequences identified herein is defined as the percentage of amino acid residues in a candidate sequence that are identical with the amino residues in the UCP5 sequence, after aligning the sequences and introducing gaps, if necessary, to achieve the maximum percent sequence identity, and not considering any conservative substitutions as part of the sequence identity. % identity can be determined by WU-BLAST-2, obtained from Altschul et al, Methods in Enzymology, 266: 460–480 (1996) blastwustl/edu/blat/README.html. WU-BLAST-2 uses several search parameters, most of which are set to the default values. The adjustable parameter are set with the following values: overlap span=1, overlap fraction=0.125, word threshold (T)=11. The HSP S and HSP S2 parameters are dynamic values and are established by the program itself depending upon the composition of die particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The term "positives", in the context of sequence comparison performed as described above, includes residues in the sequences compared that are not identical but have similar properties (e.g. as a result of conservative substitutions). The % value of positives is determined by the fraction of residues scoring a positive value in the BLOSUM 62 matrix divided by the total number of residues in the longer sequence, as defined above.

In a similar manner, "percent (%) nucleic acid sequence identity" is defined as the percentage of nucleotides in a candidate sequence that are identical with the nucleotides in the UCP5 coding sequence. The identity values can be generated by the BLASTN module of WU-BLAST-2 set to the default parameters, with overlap span and overlap fraction set to 1 and 0.125, respectively.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the UCP5 natural environment will not be present. Ordinarily, however, isolated polypeptide will be prepared by at least one purification step.

An "isolated" nucleic acid molecule encoding a UCP5 polypeptide is a nucleic acid molecule that is identified and separated from at least one contaminant nucleic acid molecule with which it is ordinarily associated in the natural source of the UCP5-encoding nucleic acid. An isolated UCP5-encoding nucleic acid molecule is other than in the form or setting in which it is found in nature. Isolated nucleic acid molecules therefore are distinguished from the UCP5-encoding nucleic acid molecule as it exists in natural cells. However, an isolated nucleic acid molecule encoding a UCP5 polypeptide includes UCP5-encoding nucleic acid molecules contained in cells that ordinarily express UCP5 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-UCP5 monoclonal antibodies (including agonist, antagonist, and neutralizing antibodies) and anti-UCP5 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 $\mu$g/ml), 0.1% SDS, and 10% dextran sulfate at 42° C., with washes at 42° C. in 0.2×SSC (sodium chloride/sodium citrate) and 50% formamide at 55° C. followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a UCP5 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of UCP5 which retain the biologic and/or immunologic activities of native or naturally-occurring UCP5. A preferred activity is the ability to affect mitochondrial membrane potential in a way that results in an up- or down-regulation of metabolic rate and/or heat production. One such activity includes the generation of proton leakage in mitochondrial membrane that results in an increase in metabolic rate.

The term "antagonist" is used in the broadest sense, and includes any molecule that partially or fully blocks, inhibits, or neutralizes a biological activity of a native UCP5 polypeptide disclosed herein. In a similar manner, the term "agonist" is used in the broadest sense and includes any molecule that mimics a biological activity of a native UCP5 polypeptide disclosed herein. Suitable agonist or antagonist molecules specifically include agonist or antagonist antibodies or antibody fragments, or fragments or amino acid sequence variants of native UCP5 polypeptides.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cows, horses, sheep, pigs, etc. Preferably, the mammal is human.

Administration "in combination with" one or more further therapeutic agents includes simultaneous (concurrent) and consecutive administration in any order.

II. Compositions and Methods of the Invention

A. Full-length UCP5

The present invention provides newly identified and isolated nucleotide sequences encoding polypeptides referred to in the present application as UCP5. In particular, cDNA encoding a UCP5 polypeptide has been identified and isolated, as disclosed in further detail in the Examples below. For sake of simplicity, in the present specification the protein encoded by DNA 80562-1663 as well as all further native homologues and variants included in the foregoing definition of UCP5, will be referred to as "UCP5, " regardless of their origin or mode of preparation.

As disclosed in the Examples below, a clone DNA 80562-1663 has been deposited with ATCC and assigned accession no. 203325. The actual nucleotide sequence of the clone can readily be determined by the skilled artisan by sequencing of the deposited clone using routine methods in the art. The predicted amino acid sequence can be determined from the nucleotide sequence using routine skill. For the UCP5 herein, Applicants have identified what is believed to be the reading frame best identifiable with the sequence information available at the time of filing.

Using Align software (GNE), it has been found that a full-length native sequence UCP5 (shown in FIG. 1 and SEQ ID NO: 1) has about 38% amino acid sequence identity with UCP3, about 36% amino acid sequence identity with UCP2, and about 33% amino acid sequence identity with UCP1.

Accordingly, it is presently believed that UCP5 disclosed in the present application is a newly identified member of the human uncoupling protein family and may possess activity(s) and/or property(s) typical of that protein family, such as the ability to enhance or supress metabolic rate by affecting mitochondrial membrane potential.

B. UCP5 Variants

In addition to the full-length native sequence UCP5 polypeptides described herein, it is contemplated that UCP5 variants can be prepared. UCP5 variants can be prepared by introducing appropriate nucleotide changes into the UCP5 DNA, and/or by synthesis of the desired UCP5 polypeptide. Those skilled in the art will appreciate that amino acid changes may alter post-translational processes of the UCP5, such as changing the number or position of glycosylation sites or altering the membrane anchoring characteristics.

Variations in the native full-length sequence UCP5 or in various domains of the UCP5 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the UCP5 that results in a change in the amino acid sequence of the UCP5 as compared with the native sequence UCP5. Optionally the variation is by substitution of at least one amino acid with any other amino acid in one or more of the domains of the UCP5. Guidance in determining which amino acid residue may be inserted, substituted or deleted without adversely affecting the desired activity may be found by comparing the sequence of the UCP5 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and, if desired, testing the resulting variants for activity in assays known in the art or as described herein.

One embodiment of the invention is directed to UCP5 variants which are fragments of the full length UCP5. Preferably, such fragments retain a desired activity or property of the full length UCP5.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the UCP5 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081–1085 (1989)]. Alanine is also typically because it is the most common amino acid. Further, it is frequently found in both buried and exposed positions [Creighton, *The Proteins*,(W. H. Freeman & Co., N.Y.); Chothia, *J. Mol. Biol.,* 150:1 (1976)]. If alanine substitution does not yield adequate amounts of variant, an isoteric amino acid can be used.

C. Modifications of UCP5

Covalent modifications of UCP5 are included within the scope of this invention. One type of covalent modification includes reacting targeted amino acid residues of a UCP5 polypeptide with an organic derivatizing agent that is capable of reacting with selected side chains or the N- or C-terminal residues of the UCP5. Derivatization with bifunctional agents is useful, for instance, for crosslinking UCP5 to a water-insoluble support matrix or surface for use in the method for purifying anti-UCP5 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the UCP5 polypeptide included within the scope of this invention comprises altering the native glycosylation pattern of the polypeptide. "Altering the native glycosylation pattern" is intended for purposes herein to mean deleting one or more carbohydrate moieties found in native sequence UCP5 (either by removing the underlying glycosylation site or by deleting the glycosylation by chemical and/or enzymatic means), and/or adding one or more glycosylation sites that are not present in the native sequence UCP5. In addition, the phrase includes qualitative changes in the glycosylation of the native proteins, involving a change in the nature and proportions of the various carbohydrate moieties present.

Addition of glycosylation sites to the UCP5 polypeptide may be accomplished by altering the amino acid sequence. The alteration may be made, for example, by the addition of, or substitution by, one or more serine or threonine residues to the native sequence UCP5 (for O-linked glycosylation sites). The UCP5 amino acid sequence may optionally be altered through changes at the DNA level, particularly by mutating the DNA encoding the UCP5 polypeptide at preselected bases such that codons are generated that will translate into the desired amino acids.

Another means of increasing the number of carbohydrate moieties on the UCP5 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259–306 (1981).

Removal of carbohydrate moieties present on the UCP5 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of UCP5 comprises linking the UCP5 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The UCP5 of the present invention may also be modified in a way to form a chimeric molecule comprising UCP5 fused to another, heterologous polypeptide or amino acid sequence.

In one embodiment, such a chimeric molecule comprises a fusion of the UCP5 with a tag polypeptide which provides an epitope to which an anti-tag antibody can selectively bind. The epitope tag is generally placed at the amino- or carboxyl- terminus of the UCP5. The presence of such epitope-tagged forms of the UCP5 can be detected using an antibody against the tag polypeptide. Also, provision of the epitope tag enables the UCP5 to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159–2165 (1988)]; the c-myc tag and the 8F9, 3C7, 6E10, G4, B7 and 9E10 antibodies thereto [Evan et al., *Molecular and Cellular Biology,* 5:3610–3616 (1985)]; and the Herpes Simplex virus glycoprotein D (gD) tag and its antibody [Paborsky et al., *Protein Engineering,* 3(6) :547–553 (1990)]. Other tag polypeptides include the Flag-peptide [Hopp et al., *BioTechnology,* 6:1204–1210 (1988)]; the KT3 epitope peptide [Martin et al., *Science,* 255:192–194 (1992)]; an α-tubulin epitope peptide [Skinner et al., *J. Biol. Chem.,* 266:15163–15166 (1991)]; and the T7 gene 10 protein peptide tag [Lutz-Freyermuth et al., *Proc. Natl. Acad. Sci. USA,* 87:6393–6397 (1990)].

In an alternative embodiment, the chimeric molecule may comprise a fusion of the UCP5 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a UCP5 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

The UCP5 of the invention may also be modified in a way to form a chimeric molecule comprising UCP5 fused to a leucine zipper. Various leucine zipper polypeptides have been described in the art. See, e.g., Landschulz et al., *Science,* 240:1759 (1988); WO 94/10308; Hoppe et al., *FEBS Letters,* 344:1991 (1994); Maniatis et al., *Nature,* 341:24 (1989). Those skilled in the art will appreciate that the leucine zipper may be fused at either the 5' or 3' end of the UCP5 molecule.

D. Preparation of UCP5

The description below relates primarily to production of UCP5 by culturing cells transformed or transfected with a vector containing UCP5 nucleic acid. It is, of course, contemplated that alternative methods, which are well known in the art, may be employed to prepare UCP5. For instance, the UCP5 sequence, or portions thereof, may be produced by direct peptide synthesis using solid-phase techniques [see, e.g., Stewart et al., *Solid-Phase Peptide Synthesis*, W. H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the UCP5 may be chemically synthesized separately and combined using chemical or enzymatic methods to produce the full-length UCP5.

1. Isolation of DNA Encoding UCP5

DNA encoding UCP5 may be obtained from a cDNA library prepared from tissue believed to possess the UCP5 mRNA and to express it at a detectable level. Accordingly, human UCP5 DNA can be conveniently obtained from a cDNA library prepared from human tissue, such as described in the Examples. The UCP5-encoding gene may also be obtained from a genomic library or by oligonucleotide synthesis.

Libraries can be screened with probes (such as antibodies to the UCP5 or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding UCP5 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra, and are described above in Section I.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as BLAST, BLAST2, ALIGN, DNAstar, and INHERIT to measure identity or positives for the sequence comparison.

Nucleic acid having protein coding sequence may be obtained by screening selected cDNA or genomic libraries using the deduced amino acid sequence disclosed herein, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for UCP5 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with Agrobacterium tumefaciens is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.(USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for UCP5-encoding vectors. *Saccharomyces cerevisiae* is a commonly used lower eukaryotic host microorganism.

Suitable host cells for the expression of glycosylated UCP5 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol, Reprod.*, 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding UCP5 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The UCP5 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the UCP5-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 μm plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the UCP5-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the UCP5-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. Promoters for use in bacterial systems also will contain a Shine-Dalgarno (S.D.) sequence operably linked to the DNA encoding UCP5.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Req.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

UCP5 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the UCP5 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the UCP5 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAS. These regions contain nucleotide segments transcribed as polyadenylated fragments in the untranslated portion of the mRNA encoding UCP5.

Still other methods, vectors, and host cells suitable for adaptation to the synthesis of UCP5 in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence UCP5 polypeptide or against a synthetic peptide based on the DNA sequences provided herein or against exogenous sequence fused to UCP5 DNA and encoding a specific antibody epitope.

5. Purification of Polypeptide

Forms of UCP5 may be recovered from culture medium or from host cell lysates. If membrane-bound, it can be released from the membrane using a suitable detergent solution (e.g. Triton-X 100) or by enzymatic cleavage. Cells employed in expression of UCP5 can be disrupted by various physical or chemical means, such as freeze-thaw cycling, sonication, mechanical disruption, or cell lysing agents.

It may be desired to purify UCP5 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the UCP5. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular UCP5 produced.

E. Uses for UCP5

Nucleotide sequences (or their complement) encoding UCP5 have various applications in the art of molecular biology, including uses as hybridization probes, in chromosome and gene mapping and in the generation of anti-sense RNA and DNA. UCP5 nucleic acid will also be useful for the preparation of UCP5 polypeptides by the recombinant techniques described herein.

The full-length native sequence UCP5 gene (SEQ ID NO: 2), or fragments thereof, may be used as, among other things, hybridization probes for a cDNA library to isolate the full-length UCP5 gene or to isolate still other genes (for instance, those encoding naturally-occurring variants of UCP5 or UCP5 from other species) which have a desired sequence identity to the UCP5 sequence disclosed in FIG. 1 (SEQ ID NO: 1). Optionally, the length of the probes will be about 20 to about 80 bases. The hybridization probes may be derived from the nucleotide sequence of SEQ ID NO: 2 or from genomic sequences including promoters, enhancer elements and introns of native sequence UCP5.By way of example, a screening method will comprise isolating the coding region of the UCP5 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the UCP5 gene of the present invention can be used to screen libraries of human cDNA, genomic DNA or mRNA to determine which members of such libraries the probe hybridizes to. Hybridization techniques are described in further detail in the Examples below.

Fragments of UCP5 DNA contemplated by the invention include sequences comprising at least about 20 to 30 consecutive nucleotides of the DNA of SEQ ID NO: 2.Preferably, such sequences comprise at least about 50 consecutive nucleotides of the DNA of SEQ ID NO: 2.

The probes may also be employed in PCR techniques to generate a pool of sequences for identification of closely related UCP5 coding sequences.

Nucleotide sequences encoding a UCP5 can also be used to construct hybridization probes for mapping the gene which encodes that UCP5 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for UCP5 encode a protein which binds to another protein, the UCP5 can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor UCP5 can be used to isolate correlative ligand(s). Screening assays can be designed to find lead compounds that mimic the biological activity of a native UCP5 or a receptor for UCP5. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode UCP5 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding UCP5 can be used to clone genomic DNA encoding UCP5 in accordance with established techniques and the genomic sequences used to generate transgenic animals that contain cells which express DNA encoding UCP5. Methods for generating transgenic animals, particularly animals such as mice or rats, have become conventional in the art and are described, for example, in U.S. Pat. Nos. 4,736,866 and 4,870,009. Typically, particular cells would be targeted for UCP5 transgene incorporation with tissue-specific enhancers. Transgenic animals that include a copy of a transgene encoding UCP5 introduced into the germ line of the animal at an embryonic stage can be used to examine the effect of increased expression of DNA encoding UCP5. Such animals can be used as tester animals for reagents thought to confer protection from, for example, pathological conditions associated with its overexpression or underexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of UCP5 can be used to construct a UCP5 "knock out" animal which has a defective or altered gene encoding UCP5 as a result of homologous recombination between the endogenous gene encoding UCP5 and altered genomic DNA encoding UCP5 introduced into an embryonic cell of the animal. For example, cDNA encoding UCP5 can be used to clone genomic DNA encoding UCP5 in accordance with established techniques. A portion of the genomic DNA encoding UCP5 can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Eryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the UCP5 polypeptide.

Nucleic acid encoding the UCP5 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnoloy* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

It is believed that the UCP5 gene therapy has applications in, for instance, treating metabolic conditions. This can be accomplished, for example, using the techniques described above and by introducing a viral vector containing a UCP5 gene into certain tissues (like muscle or fat) to increase metabolic rate in these targeted tissues and thereby elevate energy expenditure.

Generally, methods of treatment employing UCP5 are contemplated by the invention. Fuel combustion, electron transport, proton pumping and $O_2$ consumption (which may be referred to collectively as metabolic rate) are coupled to ATP synthesis. There can be an "inefficiency" in mammals, such that a portion of metabolic rate (in some cases which may be greater than 20%) may be ascribed to $H^+$ "leak" back into the matrix space with no ATP synthesis.

It is believed UCP5 may be involved in catalyzing $H^+$ leak, thereby playing a role in energetic inefficiency in vivo.

Accordingly, modulating UCP5 activity or quantities (presence or expression) of UCP5 in mammalian tissues (particularly, metabolically important tissues), may concomitantly modulate H$^+$ leak, metabolic rate and heat production. The methods of modulating (either in an up-regulation or down-regulation mode) metabolic rate in a mammal has a variety of therapeutic applications, including treatment of obesity and the symptoms associated with stroke, trauma (such as burn trauma), sepsis and infection.

In the treatment of obesity, those skilled in the art will appreciate that the modulation of mitochonrial membrane potential may be used to increase body metabolic rate, thereby enhancing an individual's ability for weight loss. Screening assays may be conducted to identify molecules which can up-regulate expression or activity (such as the uncoupling) of UCP5. The molecules thus identified can then be employed to increase metabolic rate and enhance weight loss.

UCP5 may also be employed in diagnostic methods. For example, the presence or absence of UCP5 activity, or alternatively over- or under-expression of UCP5 in an individual's cells, can be detected. The skilled practitioner may use information resulting from such detection assays to assist in predicting metabolic conditions or risk for onset of obesity. If it is determined, for instance, that UCP5 activity in a patient is abnormally high or low, therapy such as hormone therapy or gene therapy could be administered to return the UCP5 activity or expression to a physiologically acceptable state.

Detection of impaired UCP5 function in the mammal may also be used to assist in diagnosing impaired neural activity or neural degeneration. It is presently believed UCP5 may be involved in the regulation of brain temperature or metabolic rate that is required for normal brain function (and associated neural activity). It is also presently believed that UCP5 may control the generation of reactive oxygen species and therefore contribute to neural degeneration. Molecules identified in the screening assays which have been found to suppress UCP5 expression or function may also be employed to treat fever since it is believed that UCP5 is up-regulated during episodes of fever.

UCP5 has been found to be expressed in a relatively wide number of tissues and is believed to be involved in the maintenance of metabolic rate in mammals. As described in the Examples section of the application, isoforms of UCP5 are differentially expressed in human tissues and have different levels of activities in modulating mitochondrial membrane potential. An alteration of UCP5 expression or relative abundance of its isoforms in mammalian tissue(s) may lead to an alteration in metabolic rate (for instance, a lower or decreased expression of UCP5 or an alteration of UCP5 tissue distribution may be present in obese mammals). Such alteration in expression or distribution of UCP5 isoforms may also result in a predisposition to obesity in mammals.

Accordingly, the UCP5 molecules described in the application will be useful in diagnostic methods. For example, the presence or absence of UCP5 activity, or alternatively over- or under-expression, in an individual's cells or tissues, can be detected using assays known in the art, including those described in the Examples below. The invention provides a method of detecting expression of UCP5 (or its isoforms) in a mammalian cell or tissue sample, comprising contacting a mammalian cell or tissue sample with a DNA probe and analyzing expression of UCP5 mRNA transcript in said sample. Quantitative RT-PCR methods using DNA primers and probes which are isoform specific may also be employed to assist in quantitating specific isoform mRNA abundance. Further, DNA array technologies in the art may be employed to quantitate one or more isoform(s) RNA abundance. The sample may comprise various mammalian cells or tissues, including but not limited to, liver tissue, white adipose tissue and skeletal muscle. The skilled practitioner may use information resulting from such detection assays to assist in predicting metabolic conditions or onset of obesity. If it is determined, for instance, that UCP5 expression (or abundance) levels or distribution levels in a patient are abnormally high or low as compared to a control population of mammals of corresponding age and normal body weight (or alternatively, to a population of mammals diagnosed as being obese), therapy such as gene therapy, diet control, etc. may be employed to treat the mammal.

Detection of impaired UCP5 expression or function in the mammal may also be used to assist in diagnosing or treating impaired neural activity or neural degeneration. It is known in the art that reactive oxygen species can cause cellular damage in various tissues, particularly in brain tissue, and more particularly in brain neuronal tissue. An increase in the presence or generation of reactive oxygen species has been associated with Down's syndrome, as well as other neurodegenerative diseases. It is believed that UCP5 or its isoforms can regulate the generation of reactive oxygen species and may play a protective role.

Accordingly, in the treatment of the conditions described above, those skilled in the art will appreciate that the modulation of UCP5 expression or activity may be used to, for instance, increase body metabolic rate, thereby enhancing an individual's ability for weight loss. Screening assays may be conducted to identify molecules which can up-regulate expression or activity (such as the uncoupling) of UCP5. The molecules thus identified can then be employed to increase metabolic rate and enhance weight loss. The UCP5 polypeptides are useful in assays for identifying lead compounds for therapeutically active agents that modulate expression or activity of UCP5. Candidate molecules or compounds may be assayed with the mammals' cells or tissues to determine the effect(s) of the candidate molecule or compound on UCP5 expression or activity. Such screening assays may be amenable to high-throughput screening of chemical libraries, and are particularly suitable for identifying small molecule drug candidates. Small molecules include but are not limited to synthetic organic or inorganic compounds. The assays can be performed in a variety of formats, including protein-protein binding assays, biochemical screening assays, immunoassays, cell based assays, etc. Such assay formats are well known in the art.

Accordingly, in one embodiment, there is provided a method of conducting a screening assay to identify a molecule which enhances or up-regulates either activity and/or expression of UCP5, comprising the steps of exposing a mammalian cell or tissue sample believed to comprise UCP5 to a candidate molecule and subsequently analyzing expression and/or activity of UCP5 in said sample. In this method, the sample may be further analyzed for mitochondrial membrane potential. Optionally, the UCP5 is a native polypeptide or any of the specific isoforms of UCP5 identified herein. The sample being analyzed may comprise various mammalian cells or tissues, including but not limited to human brain tissue. The screening assay may be an in vitro or in vivo assay. By way of example, an in vivo screening assay may be conducted in a transgenic animal wherein a promoter for a UCP5 gene may be linked to a reporter gene such as luciferase or beta-galactosidase. Optionally, "knock in"

technology may be used in this regard in which such a reporter gene is inserted 5' to the promoter (which in turn is linked to a genomic sequence encoding a UCP5). Such techniques are known in the art. The candidate molecule employed in the screening assay may be a small molecule comprising a synthetic organic or inorganic compound. In an alternative embodiment, the screening assay is conducted to identify a molecule which decreases or down-regulates activity and/or expression of UCP5. The effect(s) that such candidate molecule may have on the expression and/or activity of UCP5 may be compared to a control or reference sample, such as for instance, expression or activity of UCP5 observed in a like mammal.

F. Anti-UCP5 Antibodies

The present invention further provides anti-UCP5 antibodies. Exemplary antibodies include polyclonal, monoclonal, humanized, bispecific, and heteroconjugate antibodies.

1. Polyclonal Antibodies

The anti-UCP5 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the UCP5 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-UCP5 antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the UCP5 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against UCP5. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-UCP5 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522–525 (1986); Riechmann et al., Nature, 332:323–329 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522–525 (1986); Riechmann et al., Nature, 332:323–327 (1988); Verhoeyen et al., Science, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779–783 (1992); Lonberg et al., Nature 368 856–859 (1994); Morrison, Nature 368, 812–13 (1994); Fishwild et al., Nature Biotechnology 14, 845–51 (1996); Neuberger, Nature Biotechnology 14, 826 (1996); Lonberg and Huszar, Intern. Rev. Immunol. 13 65–93 (1995).

4. Bispecific Antibodies

Bispecific antibodies are monoclonal, preferably human or humanized, antibodies that have binding specificities for at least two different antigens. In the present case, one of the binding specificities is for the UCP5, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for anti-UCP5 Antibodies

The anti-UCP5 antibodies of the invention have various utilities. For example, anti-UCP5 antibodies may be used in diagnostic assays for UCP5, e.g., detecting its expression in specific cells or tissues. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-UCP5 antibodies also are useful for the affinity purification of UCP5 from recombinant cell culture or natural sources. In this process, the antibodies against UCP5 are immobilized on a suitable support, such a Sephadex resin or filter paper, using methods well known in the art. The immobilized antibody then is contacted with a sample containing the UCP5 to be purified, and thereafter the support is washed with a suitable solvent that will remove substantially all the material in the sample except the UCP5, which is bound to the immobilized antibody. Finally, the support is washed with another suitable solvent that will release the UCP5 from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of cDNA clones Encoding Human UCP5

EST databases, including public EST databases (e.g., GenBank), were searched for sequences having homologies to human UCP3. The search was performed using the computer program BLAST or BLAST2 [Altschul et al., *Methods in Enzymology*, 266:460–480 (1996)] as a comparison of the UCP3 protein sequences to a 6 frame translation of the EST sequences. Those comparisons resulting in a BLAST score of 70 (or in some cases, 90) or greater that did not encode known proteins were clustered and assembled into consensus DNA sequences with the program AssemblyLIGN and MacVector (Oxford Molecular Group, Inc.).

A DNA sequence ("from DNA") was assembled relative to other EST sequences using AssemblyLIGN software (FIG. 5; SEQ ID NO: 5). ESTs from the GenBank and Merck databases used in the assembly included the sequences having the following accession nos.: R19440; AA15735; R44688; AA142931; N48177; AA056945; AA021118; AA054608; AA401224; N53324; AA057005; AA015832; AA404241; AI032869; AA910774; AI131262; AI128486; AI241428; AA021119; and AI039086. In addition, the from DNA sequence was extended using repeated cycles of BLAST and AssemblyLIGN to extend the sequence as far as possible using the sources of EST sequences discussed above.

Based on this DNA sequence, oligonucleotides were synthesized to isolate a clone of the full-length coding sequences for UCP5 by PCR. Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5kbp.

PCR primers (forward and reverse) were synthesized:
forward PCR primer GAACTGGCAAGATCCTGCTACCC (A-381V) (SEQ ID NO: 3)
reverse PCR primer GCTGGCAGGGCTGGGCTCAC (A-381W) (SEQ ID NO: 4)

RNA for construction of the cDNA libraries was isolated from human B cell, fetal kidney, and substantia nigra tissues, as well as mouse hypothalamus. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRKSB is a precursor of pRKSD that does not contain the SfiI site; see, Holmes et al., *Science*, 253:1278–1280 (1991)) in the unique XhoI and NotI sites.

Corresponding full length cDNAs were obtained by polymerase chain reaction (PCR) from the human substantia nigra library and the mouse hypothalamus cDNA library, and cloned into a mammalian expression vector pRK7 (Genentech, Inc). Eight to ten clones from each library were sequenced, among which it was noted that different clones encoded multiple isoforms.

DNA sequencing of the clones isolated by PCR as described above gave the full-length DNA sequence for human UCP5 (designated herein as DNA 80562-1663 [FIG. 1, SEQ ID NO: 2]) and the derived protein sequence for UCP5 (FIG. 1, SEQ ID NO: 1). DNA sequences of what are believed to be two other isoforms of the human UCP5 gene, hUCP5S [FIG. 12, SEQ ID NO: 6] and hUCP5SI [FIG. 13, SEQ ID NO: 8], and two isoforms, mUCP5S [FIG. 14, SEQ ID NO: 10] and mUCP5L [FIG. 15, SEQ ID NO: 12], of the mouse UCP5 gene were similarly identified. An alignment of the derived amino acid sequences for UCP5 (SEQ ID NO: 1), hUCP5S (SEQ ID NO: 7), hUCP5SI (SEQ ID NO: 9), mUCP5S (SEQ ID NO: 11)and mUCP5L (SEQ ID NO: 13) is shown in FIG. 16.

The entire coding sequence of the full length human UCP5 is shown in FIG. 1 (SEQ ID NO: 2). Clone DNA 80562-1663 contains a single open reading frame with an apparent translational initiation site at nucleotide positions 10–12, and an apparent stop codon at nucleotide positions 985–987. (See FIG. 1; SEQ ID NO: 2). The predicted polypeptide precursor is 325 amino acids long. It is presently believed that UCP5 is a membrane-bound protein and contains at least 6 transmembrane regions. MacVector software (Oxford Molecular Group, Inc.) was used to identify protein features. Transmembrane domain regions were identified at the amino acid sequence of residues 42 to 61, 103 to 117, 142 to 160, 202 to 218, 236 to 255, and 294 to 317 (using the numbering of amino acid residues according to FIG. 1 (SEQ ID NO:1)). These putative transmembrane regions in the UCP5 amino acid sequence are illustrated in FIG. 2.

The following additional features also were identified. A signal peptide was identified at the amino acid sequence of residues 1 to 19. A tyrosine kinase phosphorylation site was identified at the amino acid sequence of residues 78 to 84. Thirteen N-myristoylation sites were found at the amino acid sequence starting at residues 2, 47, 86, 106, 123, 148, 152, 178, 195, 199, 246, 249, and 278. Three mitochondrial carrier protein motifs were identified at the amino acid sequence of residues 60 to 68, 161 to 169, and 255 to 263. A unique hydrophobic amino terminal sequence (amino acids 1–23) which may be involved in membrane anchoring was also identified.

hUCP5S is shorter than UCP5, when aligned with UCP5 (FIG. 16), hUCP5S appears to be identical except that three amino acids (amino acids 23–25, as shown in FIG. 16) in its unique amino terminal portion are deleted. hUCP5SI as compared to UCP5 has a 31-amino acid insertion between transmembrane domains III and IV and lacks the three amino acid residues, 23–25 of FIG. 1 (see FIG. 16). This insertional sequence in hUCP5SI also contains a hydrophobic segment that may also be involved in interaction with the mitochondrial membrane. The hUCP5 and hUCP5S protein sequences appear to be highly conserved with the mouse sequence, with only 8 conserved amino acid changes (FIG. 16).

Clone DNA 80562, designated as DNA 80562-1663, contained in the pcDNA3 vector (Invitrogen) has been deposited with ATCC and is assigned ATCC deposit No. 203325. UCP5 polypeptide is obtained or obtainable by expressing the molecule encoded by the cDNA insert of the deposited ATCC 203325 vector. Digestion of the vector with BamHI and EcoRI restriction enzymes will yield an approximate 972 plus 34 bp insert. The full-length UCP5 protein shown in FIG. 1 has an estimated molecular weight of about 36,202 daltons and a pI of about 9.88.

An alignment of the amino acid sequence of UCP5 with UCPs 1, 2, 3, and 4 is illustrated in FIG. 2. The human UCP5 gene has been mapped to chromosome X (q23–q25).

Example 2

A. Northern Blot Analysis

Expression of UCP5 mRNA in human and mouse tissues was examined by Northern blot analysis. Human and mouse RNA blots were hybridized to a 1 kilobase $^{32}$P-labelled DNA probe based on the full length UCP5 cDNA; the probe was generated by digesting pcDNA3UCP5 (for the human blots) or pRRTmouseUCP5 (for the mouse blots) and purifying the UCP5 cDNA insert. Human adult RNA blot MTN-II (Clontech) (FIGS. 3A, 3B, 3C), PBLs (FIG. 3B), and cancer cells (FIG. 3D) were incubated with the DNA probes. As shown in FIG. 3D, the cancer cells probed included HL-60 (promyelocytic leukemia), HeLa cells, K562 (chronic myelogenous leukemia), MOLT-4 (lymphoblastic leukemia), Raji (Burkitt's lymphoma), SW480 (colorectal adenocarinoma), A549 (lung carcinoma), and G361 (melanoma). Two human brain multiple tissue Northern blots (Clontech) and a mouse multiple tissue Northern blot (Clontech) were also similarly probed with human UCP5 and mouse UCP5 cDNA probes, respectively. The blots were subsequently probed with a β-actin cDNA.

Northern analysis was performed according to manufacturer's instructions (Clontech). The blots were developed after overnight exposure to x-ray film.

As shown in FIG. 3, UCP5 mRNA transcripts were detected. Two UCP5 mRNA transcripts (approximately 1.7 and 2.4 kb) were detected in multiple human tissues and cancer cells (FIGS. 3A–D). Relatively high levels of transcript were present in human testis, brain, and heart. Further Northern blot analysis using two multiple tissue blots revealed that UCP5 transcript (1.7 kb) was present in most regions of the brain, with low levels found in spinal cord and corpus callosum (FIGS. 3E and 3F). When a mouse multiple tissue Northern blot was analyzed, mUCP5 transcripts were similarly detected in heart, brain, liver, kidney and testis (FIG. 3G).

B. Real Time Quantative RT-PCR

Total tissue RNA was extracted from various mouse tissues discussed below using total RNA Isolation reagent (Biotecx Lab, Inc., Houston, Tex.) according to the manufacturer's instructions. For real time RT-PCR, the extracted RNA was then treated with Dnase I (GIBCO BRL) to remove DNA contained in the extract. Gene expression analysis for UCP5 was performed as described in King, K. L. et al., *Endocrine,* 9:45–55 (1998) and Gibson, U. E. M. et al., *Genome Res.,* 6:995–1001 (1996). Primers and probes were designed using Primer Express Software (PE Applied Biosciences, Foster City, Calif.).

For mUCP5L:
forward primer, 5'-AAA TTT GCA ACG GCG GC-3' (SEQ ID NO: 14);
reverse primer, 5'-TCA GAC CAG ACA TTT CAT GGC T-3' (SEQ ID NO: 15);
probe, 5' (FAM)-TGA TTG TAA GCG GAC ATC AGA AAA GTT CCA CTT T-(TAMARA) 3' (SEQ ID NO: 16).
For total mouse UCP5:
Forward primer, 5'-GGG TGT GGT CCC AAC TGC T-3' (SEQ ID NO: 17);
Reverse primer, 5'TTC TTG GTA ATA TCA TAA ACG GGC A-3' (SEQ ID NO: 18);
probe, 5'(FAM)-CGT GCT GCA ATC GTT GTG GGA GTA GAG-(TAMARA)3' (SEQ ID NO: 19).
For mouse beta-actin:
forward primer, 5'-GAA ATC GTG CGT GAC ATC AAA GAG-3' (SEQ ID NO: 20);
reverse primer, 5'-CTC CTT CTG CAT CCT GTC AGC AA-3' (SEQ ID NO: 21);
probe, 5'(FAM)-CGG TTC CGA TGC CCT GAG GCT C(TAMARA)-3' (SEQ ID NO: 22).
For UCP5:
forward primer, 5'-GGA ATA ATC CTA AAT TTT CTA AGG GTG A-3' (SEQ ID NO: 23);
reverse primer, 5'-CTT TTC TGG TGT CCG CTT ACA A-3' (SEQ ID NO: 24);
probe, 5'(FAM)-TTT GCA ACG GCG GCC GTG-(TAMARA)3' (SEQ ID NO: 25).

For hUCP5SI:
forward primer, 5'-GGC TCT GTG GAG GTG CTT ATG-3' (SEQ ID NO: 26);
reverse primer, 5'-TGG GAT TAC AGG CAT GAG CC-3' (SEQ ID NO: 27);
probe, 5'(FAM)-CAA AAG CTG TTA CCG GCT GTG TGC TG-(TAMARA)3' (SEQ ID NO: 28)
For total human UCP5:
forward primer, 5'-GGA TGT TCC ATG CGC TGT T-3' (SEQ ID NO: 29);
reverse primer, 5'-CGC AGG AGC AAT TCC TGA A-3' (SEQ ID NO; 30);
probe, 5'(FAM)-CGC ATC TGT AAA GAG GAA GGT GTA TTG GCT CTC-(TAMARA)3' (SEQ ID NO: 31).

The thermal cycling conditions were as follows: 15 min at 50° C. and 10 min at 95° C., followed by 40 cycles of 95° C. for 15 sec and 60° C. for 1 min. All reactions were performed using Model 7700 Sequence Detector (PE Applied Biosciences). β-actin was used to normalize for differences in the amount of mRNA in each reaction, as its abundance was not affected by treatments. Each RNA sample was run in duplicate and the mean values of the duplicates were used to calculate the gene expression level.

For determination of tissue distribution of UCP5 in human tissues, total RNA from various human tissues (Clontech) was analyzed by a real time quantitative RT-PCR assay, with 18S mRNA used as a normalization control (primers and probes purchased from PE Applied Biosciences). The relative abundance of hUCP5S was obtained by subtraction of the UCP5 level from the total UCP5 level.

Consistent with the Northern blot analyses, abundant UCP5 mRNA was detected in human brain, testis, kidney, uterus, heart, lung, stomach, liver, and skeletal muscle, with the greatest expression in brain and testis (FIG. 3H). In mouse, UCP5 was detected in brain, testis, liver, white adipose tissue, brown adipose tissue, kidney, skeletal muscle and heart, with mUCP5S being the predominant form (FIG. 3I). The relative abundance of UCP5 and UCP5S in brain is dramatically different between human and mouse. Generally, UCP5 is more abundant in human than in mouse tissue, ranging from 12% (kidney) to 100% (brain) of the total UCP5 mRNA. Human skeletal muscle had approximately equal amounts of UCP5L and UCP5S. UCP5L is the predominant form in human brain, while 98% of the UCP5 mRNA is UCP5S in mouse brain. Further, UCP5S was predominant in all the other tissues examined. For example, 85% of the UCP5 mRNA is UCP5S in human liver, and UCP5L is detectable only in mouse brain and white adipose tissue (FIGS. 3H and 3I) A trace amount of UCP5SI was present in human substantia nigra and hippocampus, but was undetectable in all other tissues.

Example 3

Use of UCP5 as a Hybridization Probe

The following method describes use of a nucleotide sequence encoding UCP5 as a hybridization probe.

DNA comprising the coding sequence of full-length or mature UCP5 (as shown in FIG. 1, SEQ ID NO: 2) is employed as a probe to screen for homologous DNAs (such as those encoding naturally-occurring variants of UCP5) in human tissue cDNA libraries or human tissue genomic libraries.

Hybridization and washing of filters containing either library DNAs is performed under the following high stringency conditions. Hybridization of radiolabeled UCP5-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence UCP5 can then be identified using standard techniques known in the art.

Example 4

Expression of UCP5 in E. coli

This example illustrates preparation of UCP5 by recombinant expression in E. coli.

The DNA sequence encoding UCP5 (SEQ ID NO: 2) is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will optionally include sequences which encode for an antibiotic resistance gene, a trp promoter, a polyhis leader (including the first six STII codons, polyhis sequence, and enterokinase cleavage site), the UCP5 coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. If no signal sequence is present, and the expressed UCP5 is intracellular, the cell pellet obtained by the centrifugation can be solubilized using various agents known in the art, and the solubilized UCP5 protein can then be purified using a metal chelating column under conditions that allow tight binding of the protein. If a signal sequence is present, the expressed UCP5 can be obtained from the cell's periplasm or culture medium. Extraction and/or solubilization of the UCP5 polypeptides can be performed using agents and techniques known in the art. (See e.g. U.S. Pat. Nos. 5,663,304; 5,407,810).

Example 5

Expression of UCP5 in Mammalian Cells

This example illustrates preparation of UCP5 by recombinant expression in mammalian cells.

The vector, pRK5 (see EP 307,247, published Mar. 15, 1989), is employed as the expression vector. Optionally, the UCP5 DNA is ligated into pRK5 with selected restriction enzymes to allow insertion of the UCP5 DNA using ligation methods such as described in Sambrook et al., supra. The resulting vector is called pRK5-UCP5.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-UCP5 DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of UCP5 polypeptide. The cultures containing transfected cells may undergo further incubation (in serum free medium) and the medium is tested in selected bioassays.

In an alternative technique, UCP5 may be introduced into 293 cells transiently using the dextran sulfate method described by Somparyrac et al., Proc. Natl. Acad. Sci., 12:7575 (1981). 293 cells are grown to maximal density in a spinner flask and 700 μg pRK5-UCP5 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed UCP5 can then be concentrated and purified by any selected method, such as dialysis and/or column chromatography.

In another embodiment, UCP5 can be expressed in CHO cells. The pRK5-UCP5 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of UCP5 polypeptide, the culture medium may be replaced with serum free medium. Preferably, the cultures are incubated for about 6 days, and then the conditioned medium is harvested. The medium containing the expressed UCP5 can then be concentrated and purified by any selected method.

Epitope-tagged UCP5 may also be expressed in host CHO cells. The UCP5 may be subcloned out of the pRK5 vector. The subclone insert can undergo PCR to fuse in frame with a selected epitope tag such as a poly-his tag into a Baculovirus expression vector. The poly-his tagged UCP5 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged UCP5 can then be concentrated and purified by any selected method, such as by $Ni^{2+}$-chelate affinity chromatography.

In an alternative method, the UCP5 may be expressed intracellularly (where no signal sequence is employed). This intracellular expression, and subsequent extraction or solubilization and purification may be performed using techniques and reagents known in the art.

Example 6

Expression of UCP5 in Yeast

The following method describes recombinant expression of UCP5 in yeast.

First, yeast expression vectors are constructed for intracellular production or secretion of UCP5 from the ADH2/GAPDH promoter. DNA encoding UCP5 and the promoter is inserted into suitable restriction enzyme sites in the selected plasmid to direct intracellular expression of UCP5. For secretion, DNA encoding UCP5 can be cloned into the selected plasmid, together with DNA encoding the ADH2/GAPDH promoter, a native UCP5 signal peptide or other mammalian signal peptide, or, for example, a yeast alpha-factor or invertase secretory signal/leader sequence, and linker sequences (if needed) for expression of UCP5. Alternatively, the native signal sequence of UCP5 is employed.

Yeast cells, such as S. cerevisiae yeast strain AB110, can then be transformed with the expression plasmids described above and cultured in selected fermentation media as set forth, for instance, in U.S. Pat. Nos. 4,775,662 and 5,010,003. The transformed yeast supernatants can be analyzed by precipitation with 10% trichloroacetic acid and separation by SDS-PAGE, followed by staining of the gels with Coomassie Blue stain.

Recombinant UCP5 can subsequently be isolated and purified by removing the yeast cells from the fermentation medium by centrifugation and then concentrating the medium using selected cartridge filters. The concentrate containing UCP5 may further be purified using selected column chromatography resins. In an alternative method, the UCP5 may be expressed intracellularly (where no signal sequence is employed). The intracellular expression, and subsequent extraction or solubilization and purification may be performed using techniques and reagents known in the art.

Example 7

Expression of UCP5 in Baculovirus-Infected Insect Cells

The following method describes recombinant expression of UCP5 in Baculovirus-infected insect cells.

The sequence coding for UCP5 is fused upstream of an epitope tag contained within an expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding UCP5 or the desired portion of the coding sequence of UCP5 is amplified by PCR with primers complementary to the 5' and 3' regions. The 5' primer may incorporate flanking (selected) restriction enzyme sites. The product is then digested with those selected restriction enzymes and subcloned into the expression vector. The vector may contain the native signal sequence for UCP5 if secretion is desired.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged UCP5 can then be purified, for example, by $Ni^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged UCP5 are pooled and dialyzed against loading buffer.

Alternatively, purification of the IgG tagged (or Fc tagged) UCP5 can be performed using known chromatography techniques, including for instance, Protein A or protein G column chromatography.

Example 8

Measurement of Mitochondrial Membrane Potential Change Induced by UCP5

Assays were conducted to determine the effects of UCP5 expression on mitochondrial membrane potential.

Human embryonic kidney 293 cells (ATCC CCL 1573) were grown in culture medium (DMEM, 10% fetal bovine serum, 2 mM L-glutamine, 100 units/ml penicillin, 100 microgram/ml streptomycin) to 60%–80% confluence in 100-mm plates and co-transfected with 1–1.5 μg pGreen Lantern-1 (GibcoBRL) and 7.5 μg UCP5, UCP3-expressing constructs or vector control plasmid using Fugene™ 6 transfection reagent (Boehringer Mannheim; according to manufacturer's instructions). The transfected cells were harvested 24 hours post-transfection and resuspended in 1 ml culture medium containing 150 ng/ml TMRE (tetramethylrhodamine ethyl ester) and incubated for 30 minutes at 37° C. in the dark. The cells were then washed with 2 ml culture medium, resuspended in 1 ml culture medium and analyzed by flow cytometry. The transfected cells were identified based on the expression of fluorescence protein (GFP). Analyses of the samples were performed on an EPICS Elite-ESP (Beckman-Coulter). Samples were analyzed utilizing two spatially separated lasers. The primary laser was an argon-ion laser with fluorescence excitation at 531 nm. Fluorescence emission was detected at 525 nm and 575 nm, respectively. Approximately 10,000 cells were analyzed for each sample.

The results are illustrated in FIGS. 4A–4F. Expression of UCP3 in the 293 cells reduced mitochondrial membrane potential (mmp) by 45% (n=6; [±SD]=2.3%) (FIGS. 4B and 4E) in comparison to the control vector-transfected cells (FIGS. 4C and 4D). Expression of UCP5 in the 293 cells reduced mmp by 30% (n=6; [±SD]=2%) (FIGS. 4A and 4F).

UCP3 was localized to the mitochondrial membrane and an $NH_2$-Flag tag did not affect its uncoupling activity or mitochondrial localization [Mao, W. et al, FEBS Lett. 443:326–330 (1999)]. In contrast, an $NH_2$-tag completely abolished the uncoupling activity of UCP5L and its mitochondrial localization.

FIG. 17 shows the ability of different isoforms of UCP5 to reduce membrane potential. Expression of hUCP5S in the 293 cells significantly reduced mmp, but not to the extent of hUCP5L (FIG. 17C). A similar observation was made for mUCP5L and mUCP5S (FIG. 17C). hUCP5SI showed an activity comparable to that of hUCP5L (FIG. 17C). The expression of UCP5 isoforms in these transfected cells were monitored by a real time quantitative RT-PCR assay, as described above, and no differences were observed.

Example 9

Preparation of Antibodies that Bind UCP5

This example illustrates preparation of monoclonal antibodies which can specifically bind UCP5.

Techniques for producing the monoclonal antibodies are known in the art and are described, for instance, in Goding, supra. Immunogens that may be employed include purified UCP5, fusion proteins containing UCP5, and cells expressing recombinant UCP5 on the cell surface. Selection of the immunogen can be made by the skilled artisan without undue experimentation.

Mice, such as Balb/c, are immunized with the UCP5 immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-UCP5 antibodies.

After a suitable antibody titer has been detected, the animals "positive" for antibodies can be injected with a final intravenous injection of UCP5. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against UCP5. Determination of "positive" hybridoma cells secreting the desired monoclonal antibodies against UCP5 is within the skill in the art.

The positive hybridoma cells can be injected intraperitoneally into syngeneic Balb/c mice to produce ascites containing the anti-UCP5 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 10

The Expression of UCP5 mRNA in Mice Subjected to Food and Temperature Stresses

To evaluate whether UCP5 has uncoupling activity in situ important to metabolism, the amount of UCP5 mRNA produced in tissues of mice that were subjected to food and temperature stresses, i.e., metabolic challenges, was determined. Depending on the role UCP5 may have in metabolism, the amount of UCP5 mRNA produced in a tissue may vary with stresses to metabolism such as fasting, fat consumption, and exposure to temperature below room temperature.

The mice in this study were fed normal rodent chow (Purina Rodent Chow 5010; Purina, St. Louis, Mo.) and water ad libitum unless indicated otherwise. The type of mouse studied varied depending on the condition used to challenge the metabolism of the mouse studied and will be described below.

Generally, the mice studied were exposed to light 12 hours a day from 6:00 a.m. until 6:00 p.m. at which time they were exposed to dark for the following 12 hours.

The mice were sacrificed under $Co_2$ just prior to tissue harvest, which occurred in the morning between 8:00 and 12:00 a.m. unless specified otherwise. The tissues were harvested and total tissue RNA was prepared using reagents and protocols from Biotecx Lab, Houston, Tex. Although a number of tissues were collected from each mouse, the study focused on, measuring the abundance of UCP5 mRNA in the brain (because the brain has high UCP5 gene expression) and in the liver (because the liver is important to energy expenditure and metabolism). At least 5 mice/treatment were used in the studies.

Real time quantitative reverse-transcriptase polymerase chain reaction (RT-PCR), as described above, was used to determine the amount of UCP5 mRNA in the harvested tissues. RT-PCR was performed using mRNA samples. [Heid et al., *Genome Research*, 6:986–994 (1996); Gibson et al., *Genome Research*, 6:995–1001 (1996)]. Generally, to carry out real time quantitative RT-PCR, primers and probes specific to UCP5 were used (TaqMan Instrument, PE Biosciences, Foster City, Calif.). Valves were corrected for mRNA loading using β-actin mRNA abundance as loading control. The following primers and probes were used:

For liver UCP5:
  forward primer: 5'GGG TGT GGT CCC AAC TGC T3' (SEQ ID NO: 17);
  reverse primer: 5'TTC TTG GTA ATA TCA TAA ACG GGC A3' (SEQ ID NO: 18);
  probe: 5' (FAM)CGT GCT GCA ATC GTT GTG GGA GTA GAG(TAMARA)3' (SEQ ID NO: 19).

For beta-actin:
  forward primer: 5'GAA ATC GTG CGT GAC ATC AAA GAG3' (SEQ ID NO: 20);
  reverse primer: 5' CTC CTT CTG CAT CCT GTC AGC AA3' (SEQ ID NO: 21);
  probe: 5'(FAM)CGG TTC CGA TGC CCT GAG GCT C(TAMARA)3' (SEQ ID NO: 22).

The Effect of Food Consumption on UCP5 mRNA Expression

In a first study, seven-week old male mice (C57BL/6J; Bar Harbor, Me.) were studied to evaluate the effect of fasting and eating meals on UCP5 mRNA production in the mice studied. The mice were obtained at six weeks of age and at seven weeks were randomly assigned to one of three groups: control mice fed ad lib, mice fasted for 24 hours, and mice fasted for 24 hours and then fed ad lib for 24 hours.

The mice were sacrificed as described above after ad lib feeding for the first group, after 24 hours of fasting for the second group, and after the 48 hours of first fasting and then ad lib feeding for the third group. The tissues were harvested as described above.

Quantitative RT-PCR was performed for brain and liver tissues according to the methods described above and the amount of UCP5 mRNA produced in the brain and liver was quantified. Statistical differences across the groups were determined using a protected Fisher's least significant difference analysis (L. Ott, *An Introduction to Statistical Methods and Data Analysis*, 3rd Ed., Boston: PWS-Kent Publishing Co., 1988). The data presented in FIGS. 6A to 6C and 7A to 7C represent means +/− SEM. An asterisk indicates a statistical difference of at least $p<0.05$.

The results obtained for the brain tissue are illustrated in FIGS. 6A to 6C, and the results obtained for the liver tissue are illustrated in FIGS. 7A to 7C.

FIGS. 6A and 7A illustrate the UCP5 mRNA abundance in the brain tissue and liver tissue, respectively, from mice that were fed ad lib. FIGS. 6B and 7B illustrate the UCP5 mRNA abundance in the brain tissue and liver tissue, respectively, from mice that fasted for 24 hours. FIGS. 6C and 7C illustrate the UCP5 mRNA abundance in the brain tissue and liver tissue, respectively, from mice that fasted for 24 hours and then were fed ad lib for 24 hours.

Typically, fasting and restriction of food consumption lower metabolic rate, suggesting that expression of UCP5 mRNA would decrease for mice that were fasting compared to mice that were fed ad lib. FIG. 7B indicates a decrease in UCP5 mRNA expression in liver tissue for the mice that fasted compared to the mice that were fed ad lib as shown in FIG. 7A or the mice that were fed after fasting as shown in FIG. 7C.

The Effect of Fat Consumption on UCP5 mRNA Expression

In a second study, four-week old male mice (A/J or C57BL/6J; Jackson Labs, Bar Harbor, Me.) were studied to evaluate the effect of high and low fat diets on UCP5 mRNA production in the mice studied.

The mice were obtained at four weeks of age and immediately placed on either a low fat diet or high fat diet (Research Diets, Inc., New Brunswick, N.J.) patterned after those formulated by Surwit et al., *Metabolism*. 44(5): 645–651 (1995), containing 11% or 58% fat (% calories), respectively. Animals were fed ad lib for approximately three weeks (days 22–23 on diet). They were then sacrificed, and their tissues were harvested as described above. Quantitative RT-PCR was performed for the brain and liver tissue according to the methods described above and the amount of UCP5 mRNA produced in the brain and liver tissues was quantified. Statistical differences across the groups were determined using a protected Fisher's least significant difference analysis (L. Ott, *An Introduction to Statistical Methods and Data Analysis,* 3rd Ed., Boston: PWS-Kent Publishing Co., 1988). The data presented in FIGS. 8A to 8D and 9A to 9D represent means +/− SEM. An asterisk indicates a statistical difference of at least p<0.05.

The results obtained for the brain tissue are illustrated in FIGS. 8A to 8D, and the results obtained for the liver tissue are illustrated in FIGS. 9A to 9D.

Figures 8A, 8B, 8C, 8D, 9A, 9B, 9C, 9D:
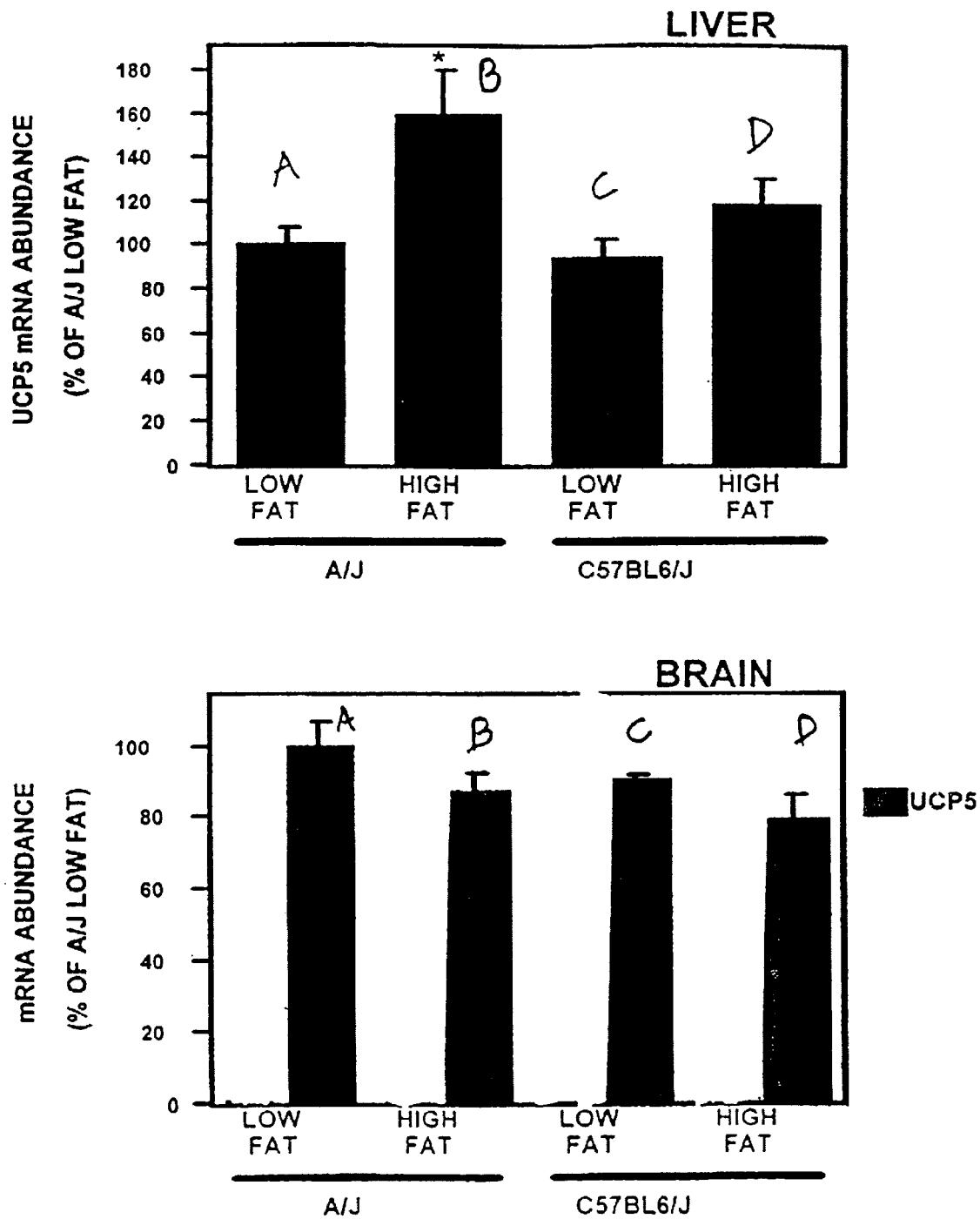
FIGS. 8A–8D show the results of in vitro assays conducted to determine the effect of fat consumption on the expression of UCP5 mRNA in brain tissue.
FIGS. 9A–9D show the results of in vitro assays conducted to determine the effect of fat consumption on the expression of UCP5 mRNA in liver tissue.

FIGS. 8A and 9A illustrate the UCP5 mRNA abundance in brain and liver tissue, respectively, from A/J mice that were fed a low fat diet, and FIGS. 8B and 9B illustrate the UCP5 mRNA abundance in brain tissue and liver tissue, respectively, from A/J mice that were fed a high fat diet. FIGS. 8C and 9C illustrate the UCP5 mRNA abundance in brain tissue and liver tissue, respectively, from C57BL6/J mice that were fed a low fat diet. FIGS. 8D and 9D illustrate the UCP5 mRNA abundance in brain tissue and liver tissue, respectively, from C57BL6/J mice that were fed a high fat diet.

A/J mice have been shown to be "obesity-resistant" on a high fat diet compared to "obesity-prone" C57BL6/J (see Surwit et al., supra). This may be due to a lower metabolic efficiency in the A/J strain-i.e., they apparently put on fewer calories per calories ingested. FIG. 9B indicates an increase in UCP5 mRNA expression in liver tissue from A/J mice fed a high fat diet compared to A/J mice fed a low fat diet as shown in FIG. 9A. Similar results for liver UCP5 mRNA expression were not obtained for the "obesity prone" C57BL6/J mice (FIGS. 9C and 9D), and similar results were not obtained for the brain tissue from either A/J mice (FIGS. 8A and 8B) or C57BL6/J mice (FIGS. 8C and 8D).

The Effect of Temperature Stress on UCP5

In a third study, male mice (FVB-N; Taconic, Germantown, N.Y.) were studied to evaluate the effect of exposing the mice to temperature stresses. Typically, cold exposure in rodents elicits an increase in metabolic rate. This metabolic increase may be to support a stable body temperature. Yet warm-acclimation, which is defined as chronic exposure to temperatures within the murine thermoneutral zone (approx. 30–35° C.), lowers metabolic rate. [Klaus et al., *Am. J. Physiol.,* 274:R287–R293 (1998)].

The mice in this study were housed two per cage and were randomly assigned to the following groups: a control group (housed at 22° C. for 3 weeks), a warm-acclimated group (housed at 33° C. for 3 weeks), a food-restricted group (housed at 22° C. for 3 weeks, but given access each day to the average amount of food eaten by warm-acclimated mice the day before), a cold-challenged group (housed at 22° C. for 3 weeks prior to the initiation of exposure to 4° C.). For the cold-challenged mice, beginning in the morning, mice were exposed to 4° C. by being placed into a 40C room for 1, 6, 24, or 48 hours prior to sacrificing the mice and harvesting the tissue.

The mice were sacrificed and tissues were harvested at six week of age as described above. Quantitative RT-PCR was performed for the brain and liver tissues according to the methods described above and the amount of UCP5 mRNA produced in the brain and liver tissues was quantified. Statistical differences across the groups were determined using a protected Fisher's least significant difference analysis (L. Ott, *An Introduction to Statistical Methods and Data Analysis,* 3rd Ed., Boston: PWS-Kent Publishing Co., 1988). The data presented in FIGS. 10A to 10G and 11A to 11G represent +/− SEM. An asterisk indicates a statistical difference of at least p<0.05.

The results obtained for the brain tissue are illustrated in FIGS. 10A to 10G, and the results obtained for the liver tissue are illustrated in FIGS. 11A to 11G.

FIGS. 10A and 11A illustrate the UCP5 mRNA abundance in the control group of mice. FIGS. 10B to 10E and 11B to 11E illustrate the UCP5 mRNA abundance in the brain tissue and liver tissue, respectively, from the group of mice that were cold-challenged for 1, 6, 24, and 48 hours, respectively. FIGS. 10F and 11F illustrate the UCP5 mRNA abundance in the brain tissue and liver tissue, respectively, from the food-restricted group of mice, and FIGS. 10G and 11G illustrate the UCP5 mRNA abundance in the brain tissue and liver tissue, respectively, from the warm-acclimated group of mice.

Deposit of Material

The following materials have been deposited with the American Type Culture Collection, 10801 University Blvd., Manassas, Va. 20110-2209, USA (ATCC):

| Material | ATCC Dep. No. | Deposit Date |
| --- | --- | --- |
| DNA80562-1663 | 203325 | Oct. 6, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC '122 and the Commissioner's rules pursuant thereto (including 37 CFR '1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated nucleic acid molecule comprising (a) a DNA molecule encoding an uncoupling protein 5 (UCP5) polypeptide comprising the sequence of amino acid residues from about 1 to about 325 of FIG. 1 (SEQ ID NO: 1), or (b) the complement of the DNA molecule of (a).

2. The isolated nucleic acid molecule of claim 1 comprising the sequence of nucleotide positions from about 10 to about 987 of FIG. 1 (SEQ ID NO: 2).

3. An isolated nucleic acid molecule comprising a sequence of FIG. 1 (SEQ ID NO: 2).

4. An isolated nucleic acid molecule encoding an uncoupling protein 5 (UCP5) polypeptide, comprising DNA hybridizing under moderately stringent conditions to the complement of the nucleic acid comprising the sequence of nucleotide positions from about 10 to about 987 of FIG. 1 (SEQ ID NO: 2).

5. A vector comprising the nucleic acid of claim 1.

6. The vector of claim 5 operably linked to control sequences recognized by a host cell transformed with the vector.

7. A host cell composing the vector of claim 5.

8. The host cell of claim 7, wherein said cell is a CHO cell.

9. The host cell of claim 7, wherein said cell is an *E. coli*.

10. The host cell of claim 7, wherein said cell is a yeast cell.

11. A vector comprising the nucleic acid of claim 3.

12. The vector of claim 11 operably linked to control sequences recognized by a host cell transformed with the vector.

13. A host cell comprising the vector of claim 12.

14. The host cell of claim 13, wherein said cell is a CHO cell.

15. The host cell of claim 13, wherein said cell is an *E. coli*.

16. The host cell of claim 13, wherein said cell is a yeast cell.

17. An isolated nucleic acid molecule comprising DNA encoding the same mature polypeptide encoded by the human uncoupling protein 5 (UCP5) cDNA in ATCC Deposit No. 203325 (DNA 80562-1663).

* * * * *

SEQUENCE LISTING

<160> NUMBER OF SEQ ID NOS: 36

<210> SEQ ID NO 1
<211> LENGTH: 325
<212> TYPE: PRT
<213> ORGANISM: Homo Sapien

<400> SEQUENCE: 1

```
Met Gly Ile Phe Pro Gly Ile Ile Leu Ile Phe Leu Arg Val Lys
 1               5                  10                  15

Phe Ala Thr Ala Ala Val Ile Val Ser Gly His Gln Lys Ser Thr
                20                  25                  30

Thr Val Ser His Glu Met Ser Gly Leu Asn Trp Lys Pro Phe Val
                35                  40                  45

Tyr Gly Gly Leu Ala Ser Ile Val Ala Glu Phe Gly Thr Phe Pro
                50                  55                  60

Val Asp Leu Thr Lys Thr Arg Leu Gln Val Gln Gly Gln Ser Ile
                65                  70                  75

Asp Ala Arg Phe Lys Glu Ile Lys Tyr Arg Gly Met Phe His Ala
                80                  85                  90

Leu Phe Arg Ile Cys Lys Glu Glu Gly Val Leu Ala Leu Tyr Ser
                95                  100                 105

Gly Ile Ala Pro Ala Leu Leu Arg Gln Ala Ser Tyr Gly Thr Ile
                110                 115                 120

Lys Ile Gly Ile Tyr Gln Ser Leu Lys Arg Leu Phe Val Glu Arg
                125                 130                 135

Leu Glu Asp Glu Thr Leu Leu Ile Asn Met Ile Cys Gly Val Val
                140                 145                 150

Ser Gly Val Ile Ser Ser Thr Ile Ala Asn Pro Thr Asp Val Leu
                155                 160                 165

Lys Ile Arg Met Gln Ala Gln Gly Ser Leu Phe Gln Gly Ser Met
                170                 175                 180

Ile Gly Ser Phe Ile Asp Ile Tyr Gln Gln Glu Gly Thr Arg Gly
                185                 190                 195

Leu Trp Arg Gly Val Val Pro Thr Ala Gln Arg Ala Ala Ile Val
                200                 205                 210

Val Gly Val Glu Leu Pro Val Tyr Asp Ile Thr Lys Lys His Leu
                215                 220                 225

Ile Leu Ser Gly Met Met Gly Asp Thr Ile Leu Thr His Phe Val
                230                 235                 240

Ser Ser Phe Thr Cys Gly Leu Ala Gly Ala Leu Ala Ser Asn Pro
                245                 250                 255

Val Asp Val Val Arg Thr Arg Met Met Asn Gln Arg Ala Ile Val
                260                 265                 270

Gly His Val Asp Leu Tyr Lys Gly Thr Val Asp Gly Ile Leu Lys
                275                 280                 285

Met Trp Lys His Glu Gly Phe Phe Ala Leu Tyr Lys Gly Phe Trp
                290                 295                 300

Pro Asn Trp Leu Arg Leu Gly Pro Trp Asn Ile Ile Phe Phe Ile
                305                 310                 315

Thr Tyr Glu Gln Leu Lys Arg Leu Gln Ile
                320                 325
```

<210> SEQ ID NO 2
<211> LENGTH: 993
<212> TYPE: DNA
<213> ORGANISM: Homo Sapien

<400> SEQUENCE: 2

| | | | | |
|---|---|---|---|---|
| ggatccgcca | tgggtatctt | tcccggaata | atcctaattt | ttctaagggt | 50 |
| gaagtttgca | acggcggccg | tgattgtaag | cggacaccag | aaaagtacca | 100 |
| ctgtaagtca | tgagatgtct | ggtctgaatt | ggaaacccct | tgtatatggc | 150 |
| ggccttgcct | ctatcgtggc | tgagtttggg | actttcctg | tggaccttac | 200 |
| caaaacacga | cttcaggttc | aaggccaaag | cattgatgcc | cgtttcaaag | 250 |
| agataaaata | tagagggatg | ttccatgcgc | tgtttcgcat | ctgtaaagag | 300 |
| gaaggtgtat | tggctctcta | ttcaggaatt | gctcctgcgt | tgctaagaca | 350 |
| agcatcatat | ggcaccatta | aaattgggat | ttaccaaagc | ttgaagcgct | 400 |
| tattcgtaga | acgtttagaa | gatgaaactc | ttttaattaa | tatgatctgt | 450 |
| ggggtagtgt | caggagtgat | atcttccact | atagccaatc | ccaccgatgt | 500 |
| tctaaagatt | cgaatgcagg | ctcaaggaag | cttgttccaa | gggagcatga | 550 |
| ttggaagctt | tatcgatata | taccaacaag | aaggcaccag | gggtctgtgg | 600 |
| aggggtgtgg | ttccaactgc | tcagcgtgct | gccatcgttg | taggagtaga | 650 |
| gctaccagtc | tatgatatta | ctaagaagca | tttaatattg | tcaggaatga | 700 |
| tgggcgatac | aattttaact | cacttcgttt | ccagctttac | atgtggtttg | 750 |
| gctgggggctc | tggcctccaa | cccggttgat | gtggttcgaa | ctcgcatgat | 800 |
| gaaccagagg | gcaatcgtgg | gacatgtgga | tctctataag | ggcactgttg | 850 |
| atggtattt | aaagatgtgg | aaacatgagg | gcttttttgc | actctataaa | 900 |
| ggattttggc | caaactggct | tcggcttgga | ccctggaaca | tcattttttt | 950 |
| tattacatac | gagcagctaa | agaggcttca | aatctaagaa | ttc | 993 |

<210> SEQ ID NO 3
<211> LENGTH: 23
<212> TYPE: DNA
<213> ORGANISM: Artificial
<220> FEATURE:
<221> NAME/KEY: Misc_feature
<222> LOCATION: 1-23
<223> OTHER INFORMATION: sequence is synthesized

<400> SEQUENCE: 3
gaactggcaa gatcctgcta ccc                                          23

<210> SEQ ID NO 4
<211> LENGTH: 20
<212> TYPE: DNA
<213> ORGANISM: Artificial
<220> FEATURE:
<221> NAME/KEY: Misc_feature
<222> LOCATION: 1-20
<223> OTHER INFORMATION: sequence is synthesized

<400> SEQUENCE: 4
gctggcaggg ctgggctcac                                              20

<210> SEQ ID NO 5
<211> LENGTH: 978
<212> TYPE: DNA

<213> ORGANISM: Artificial
<220> FEATURE:
<221> NAME/KEY: Misc_feature
<222> LOCATION: 1-978
<223> OTHER INFORMATION: sequence is synthesized

<400> SEQUENCE: 5

| | |
|---|---|
| atgggtatct tccccggaat aatcctaatt tttctaaggg tgaagtttgc | 50 |
| aacggcggcc gtgattgtaa gcggacacca gaaaagtacc actgtaagtc | 100 |
| atgagatgtc tggtctgaat tggaaaccct ttgtatatgg cggccttgcc | 150 |
| tctatcgtgg ctgagtttgg gactttccct gtggacctta ccaaaacacg | 200 |
| acttcaggtt caaggccaaa gcattgatgc ccgtttcaaa gagataaaat | 250 |
| atagagggat gttccatgcg ctgtttcgca tctgtaaaga ggaaggtgta | 300 |
| ttggctctct attcaggaat tgctcctgcg ttgctaagac aagcatcata | 350 |
| tggcaccatt aaaattggga tttaccaaag cttgaagcgc ttattcgtag | 400 |
| aacgtttaga agatgaaact cttttaatta atatgatctg tggggtagtg | 450 |
| tcaggagtga tatcttccac tatagccaat cccaccgatg ttctaaagat | 500 |
| tcgaatgcag gctcaaggaa gcttgttcca agggagcatg attggaagct | 550 |
| ttatcgatat ataccaacaa gaaggcacca ggggtctgtg gagggtgtg | 600 |
| gttccaactg ctcagcgtgc tgccatcgtt gtaggagtag agctaccagt | 650 |
| ctatgatatt actaagaagc atttaatatt gtcaggaatg atgggcgata | 700 |
| caattttaac tcacttcgtt tccagcttta catgtggttt ggctggggct | 750 |
| ctggcctcca acccggttga tgtggttcga actcgcatga tgaaccagag | 800 |
| ggcaatcgtg ggacatgtgg atctctataa gggcactgtt gatggtattt | 850 |
| taaagatgtg gaaacatgag ggcttttttg cactctataa aggattttgg | 900 |
| ccaaactggc ttcggcttgg accctggaac atcatttttt ttattacata | 950 |
| cgagcagcta agaggcttc aaatctaa | 978 |

<210> SEQ ID NO 6
<211> LENGTH: 1009
<212> TYPE: DNA
<213> ORGANISM: Homo Sapien

<400> SEQUENCE: 6

| | |
|---|---|
| atgggtatct tccccggaat aatcctaatt tttctaaggg tgaagtttgc | 50 |
| aacggcggcc gtgattcacc agaaaagtac cactgtaagt catgagatgt | 100 |
| ctggtctgaa ttggaaaccc tttgtatatg cggccttgc tctatcgtg | 150 |
| gctgagtttg ggactttccc tgtggacctt accaaaacac gacttcaggt | 200 |
| tcaaggccaa agcattgatg cccgtttcaa agagataaaa tatagaggga | 250 |
| tgttccatgc gctgtttcgc atctgtaaag aggaaggtgt attggctctc | 300 |
| tattcaggaa ttgctcctgc gttgctaaga caagcatcat atggcaccat | 350 |
| taaaattggg atttaccaaa gcttgaagcg cttattcgta gaacgtttag | 400 |
| aagatgaaac tcttttaatt aatatgatct gtggggtagt gtcaggagtg | 450 |
| atatcttcca ctatagccaa tcccaccgat gttctaaaga ttcgaatgca | 500 |
| ggctcaagga agcttgttcc aagggagcat gattggaagc tttatcgata | 550 |
| tataccaaca agaaggcacc aggggtctgt ggagggtgt ggttccaact | 600 |

```
gctcagcgtg ctgccatcgt tgtaggagta gagctaccag tctatgatat         650
tactaagaag catttaatat tgtcaggaat gatgggcgat acaattttaa         700
ctcacttcgt ttccagcttt acatgtggtt tggctggggc tctggcctcc         750
aacccggttg atgtggttcg aactcgcatg atgaaccaga gggcaatcgt         800
gggacatgtg gatctctata agggcactgt tgatggtatt ttaaagatgt         850
ggaaacatga gggcttttttt gcactctata aaggattttg gccaaactgg        900
cttcggcttg gaccctggaa catcattttt tttattacat acgagcagct         950
aaagaggctt caaatctaag aattcaatcg atggccgcca tggcccaact        1000
tgtttattg                                                     1009
```

<210> SEQ ID NO 7
<211> LENGTH: 322
<212> TYPE: PRT
<213> ORGANISM: Homo Sapien

<400> SEQUENCE: 7

```
Met Gly Ile Phe Pro Gly Ile Ile Leu Ile Phe Leu Arg Val Lys
  1               5                  10                  15

Phe Ala Thr Ala Ala Val Ile His Gln Lys Ser Thr Thr Val Ser
                 20                  25                  30

His Glu Met Ser Gly Leu Asn Trp Lys Pro Phe Val Tyr Gly Gly
                 35                  40                  45

Leu Ala Ser Ile Val Ala Glu Phe Gly Thr Phe Pro Val Asp Leu
                 50                  55                  60

Thr Lys Thr Arg Leu Gln Val Gln Gly Gln Ser Ile Asp Ala Arg
                 65                  70                  75

Phe Lys Glu Ile Lys Tyr Arg Gly Met Phe His Ala Leu Phe Arg
                 80                  85                  90

Ile Cys Lys Glu Glu Gly Val Leu Ala Leu Tyr Ser Gly Ile Ala
                 95                 100                 105

Pro Ala Leu Leu Arg Gln Ala Ser Tyr Gly Thr Ile Lys Ile Gly
                110                 115                 120

Ile Tyr Gln Ser Leu Lys Arg Leu Phe Val Glu Arg Leu Glu Asp
                125                 130                 135

Glu Thr Leu Leu Ile Asn Met Ile Cys Gly Val Val Ser Gly Val
                140                 145                 150

Ile Ser Ser Thr Ile Ala Asn Pro Thr Asp Val Leu Lys Ile Arg
                155                 160                 165

Met Gln Ala Gln Gly Ser Leu Phe Gln Gly Ser Met Ile Gly Ser
                170                 175                 180

Phe Ile Asp Ile Tyr Gln Gln Glu Gly Thr Arg Gly Leu Trp Arg
                185                 190                 195

Gly Val Val Pro Thr Ala Gln Arg Ala Ala Ile Val Val Gly Val
                200                 205                 210

Glu Leu Pro Val Tyr Asp Ile Thr Lys Lys His Leu Ile Leu Ser
                215                 220                 225

Gly Met Met Gly Asp Thr Ile Leu Thr His Phe Val Ser Ser Phe
                230                 235                 240

Thr Cys Gly Leu Ala Gly Ala Leu Ala Ser Asn Pro Val Asp Val
                245                 250                 255

Val Arg Thr Arg Met Met Asn Gln Arg Ala Ile Val Gly His Val
```

```
                260             265             270
Asp Leu Tyr Lys Gly Thr Val Asp Gly Ile Leu Lys Met Trp Lys
            275                 280                 285

His Glu Gly Phe Phe Ala Leu Tyr Lys Gly Phe Trp Pro Asn Trp
            290                 295                 300

Leu Arg Leu Gly Pro Trp Asn Ile Ile Phe Phe Ile Thr Tyr Glu
            305                 310                 315

Gln Leu Lys Arg Leu Gln Ile
            320         322

<210> SEQ ID NO 8
<211> LENGTH: 1103
<212> TYPE: DNA
<213> ORGANISM: Homo Sapien

<400> SEQUENCE: 8
atgggtatct tcccggaat  aatcctaatt tttctaaggg tgaagtttgc         50
aacggcggcc gtgattcacc agaaaagtac cactgtaagt catgagatgt        100
ctggtctgaa ttgaaaccc  tttgtatatg gcggccttgc ctctatcgtg        150
gctgagtttg ggactttccc tgtggacctt accaaaacac gacttcaggt        200
tcaaggccaa agcattgatg cccgtttcaa agagataaaa tatagaggga        250
tgttccatgc gctgtttcgc atctgtaaag aggaaggtgt attggctctc        300
tattcaggaa ttgctcctgc gttgctaaga caagcatcat atggcaccat        350
taaaattggg atttaccaaa gcttgaagcg cttattcgta gaacgtttag        400
aagatgaaac tcttttaatt aatatgatct gtggggtagt gtcaggagtg        450
atatcttcca ctatagccaa tcccaccgat gttctaaaga ttcgaatgca        500
ggctcaagga agcttgttcc aagggagcat gattggaagc tttatcgata        550
tataccaaca agaaggcacc aggggtctgt ggaggtgctt atgttcaaaa        600
gctgttaccg gctgtgtgct gtggctcatg cctgtaatcc cagcactttg        650
ggaggccaac gcgggtggat cacttgaggg tgtggttcca actgctcagc        700
gtgctgccat cgttgtagga gtagagctac cagtctatga tattactaag        750
aagcatttaa tattgtcagg aatgatgggc gatacaattt taactcactt        800
cgtttccagc tttacatgtg gtttggctgg ggctctggcc tccaacccgg        850
ttgatgtggt tcgaactcgc atgatgaacc agagggcaat cgtgggacat        900
gtggatctct ataagggcac tgttgatggt atttttaaga gtggaaaca         950 tgagggcttt tttgcactct ataaaggatt ttggccaaac tggcttcggc       1000
ttggaccctg gaacatcatt tttttttatta catacgagca gctaaagagg       1050
cttcaaatct aagaattcaa tcgatggccg ccatggccca acttgttata       1100
atg                                                         1103

<210> SEQ ID NO 9
<211> LENGTH: 353
<212> TYPE: PRT
<213> ORGANISM: Homo Sapien

<400> SEQUENCE: 9

Met Gly Ile Phe Pro Gly Ile Ile Leu Ile Phe Leu Arg Val Lys
 1               5                  10                  15
```

-continued

Phe Ala Thr Ala Ala Val Ile His Gln Lys Ser Thr Thr Val Ser
                20                  25                  30

His Glu Met Ser Gly Leu Asn Trp Lys Pro Phe Val Tyr Gly Gly
            35                  40                  45

Leu Ala Ser Ile Val Ala Glu Phe Gly Thr Phe Pro Val Asp Leu
        50                  55                  60

Thr Lys Thr Arg Leu Gln Val Gln Gly Gln Ser Ile Asp Ala Arg
    65                  70                  75

Phe Lys Glu Ile Lys Tyr Arg Gly Met Phe His Ala Leu Phe Arg
80                  85                  90

Ile Cys Lys Glu Glu Gly Val Leu Ala Leu Tyr Ser Gly Ile Ala
                95                  100                 105

Pro Ala Leu Leu Arg Gln Ala Ser Tyr Gly Thr Ile Lys Ile Gly
            110                 115                 120

Ile Tyr Gln Ser Leu Lys Arg Leu Phe Val Glu Arg Leu Glu Asp
        125                 130                 135

Glu Thr Leu Leu Ile Asn Met Ile Cys Gly Val Val Ser Gly Val
    140                 145                 150

Ile Ser Ser Thr Ile Ala Asn Pro Thr Asp Val Leu Lys Ile Arg
155                 160                 165

Met Gln Ala Gln Gly Ser Leu Phe Gln Gly Ser Met Ile Gly Ser
                170                 175                 180

Phe Ile Asp Ile Tyr Gln Gln Glu Gly Thr Arg Gly Leu Trp Arg
            185                 190                 195

Cys Leu Cys Ser Lys Ala Val Thr Gly Cys Val Leu Trp Leu Met
        200                 205                 210

Pro Val Ile Pro Ala Leu Trp Glu Ala Asn Ala Gly Gly Ser Leu
    215                 220                 225

Glu Gly Val Val Pro Thr Ala Gln Arg Ala Ala Ile Val Val Gly
230                 235                 240

Val Glu Leu Pro Val Tyr Asp Ile Thr Lys Lys His Leu Ile Leu
                245                 250                 255

Ser Gly Met Met Gly Asp Thr Ile Leu Thr His Phe Val Ser Ser
            260                 265                 270

Phe Thr Cys Gly Leu Ala Gly Ala Leu Ala Ser Asn Pro Val Asp
        275                 280                 285

Val Val Arg Thr Arg Met Met Asn Gln Arg Ala Ile Val Gly His
    290                 295                 300

Val Asp Leu Tyr Lys Gly Thr Val Asp Gly Ile Leu Lys Met Trp
305                 310                 315

Lys His Glu Gly Phe Phe Ala Leu Tyr Lys Gly Phe Trp Pro Asn
                320                 325                 330

Trp Leu Arg Leu Gly Pro Trp Asn Ile Ile Phe Phe Ile Thr Tyr
            335                 340                 345

Glu Gln Leu Lys Arg Leu Gln Ile
    350                 353

<210> SEQ ID NO 10
<211> LENGTH: 1022
<212> TYPE: DNA
<213> ORGANISM: Mus Musculus

<400> SEQUENCE: 10
ctgcaggtcg actctagagg atccgaaatg ggtatctttc ccggaataat        50

-continued

| | |
|---|---|
| cctaattttt ctaagggtga agtttgcaac ggcggcagtg attcatcaga | 100 |
| aaagttccac tttaagccat gagatgtctg gtctgaactg gaaaccttt | 150 |
| gtgtatggcg gccttgcctc tattgttgcc gagttcggca ctttccctgt | 200 |
| ggatcttact aaaacacggc tgcaagtcca aggccagagt atcgatgttc | 250 |
| gtttcaaaga aataaaatat agagggatgt tcatgccctt gttccgaatc | 300 |
| tataagaag aagggatctt ggctctgtat tcaggaattc ccctgcgtt | 350 |
| actaagacag gcatcatatg gcaccatcaa aattggtatt tatcaaagct | 400 |
| tgaagcgatt atttgtagaa cgtttggaag atgagactct cctaattaac | 450 |
| atgatctgtg gggtagtgtc aggagtgatt tcctctacta ttgccaatcc | 500 |
| cactgatgtt ctaaagattc gaatgcaggc tcaaggaagt tgttccaag | 550 |
| ggagcatgat tggcagcttc attgacatat accagcaaga aggtaccagg | 600 |
| ggtctgtgga gggtgtggt cccaactgct cagcgtgctg caatcgttgt | 650 |
| gggagtagag ctgcccgttt atgatattac caagaagcac ctgatagttt | 700 |
| caggaatgct gggagacaca attttaacac actttgtttc cagtttcacc | 750 |
| tgtggtttgg ctggggctct ggcatctaac cctgtggatg tggtgagaac | 800 |
| tcgaatgatg aatcagaggg caatagtggg acatgtggac ctctacaagg | 850 |
| gtactttgga tggtatttta agatgtggaa agcatgaggg atttttgca | 900 |
| ctctataaag gattttggcc aaactggctt cgacttggac cctggaacat | 950 |
| cattttttt attacctatg agcagctcaa gaggcttcag atctaagaat | 1000 |
| tcaatcgatg gccgccatgg cc | 1022 |

<210> SEQ ID NO 11
<211> LENGTH: 322
<212> TYPE: PRT
<213> ORGANISM: Mus Musculus

<400> SEQUENCE: 11

Met Gly Ile Phe Pro Gly Ile Ile Leu Ile Phe Leu Arg Val Lys
 1               5                  10                  15

Phe Ala Thr Ala Ala Val Ile His Gln Lys Ser Ser Thr Leu Ser
                20                  25                  30

His Glu Met Ser Gly Leu Asn Trp Lys Pro Phe Val Tyr Gly Gly
                35                  40                  45

Leu Ala Ser Ile Val Ala Glu Phe Gly Thr Phe Pro Val Asp Leu
                50                  55                  60

Thr Lys Thr Arg Leu Gln Val Gln Gly Gln Ser Ile Asp Val Arg
                65                  70                  75

Phe Lys Glu Ile Lys Tyr Arg Gly Met Phe His Ala Leu Phe Arg
                80                  85                  90

Ile Tyr Lys Glu Glu Gly Ile Leu Ala Leu Tyr Ser Gly Ile Ala
                95                  100                 105

Pro Ala Leu Leu Arg Gln Ala Ser Tyr Gly Thr Ile Lys Ile Gly
                110                 115                 120

Ile Tyr Gln Ser Leu Lys Arg Leu Phe Val Glu Arg Leu Glu Asp
                125                 130                 135

Glu Thr Leu Leu Ile Asn Met Ile Cys Gly Val Val Ser Gly Val
                140                 145                 150

Ile Ser Ser Thr Ile Ala Asn Pro Thr Asp Val Leu Lys Ile Arg

|  |  | 155 |  |  | 160 |  |  | 165 |  |
|---|---|---|---|---|---|---|---|---|---|

Met Gln Ala Gln Gly Ser Leu Phe Gln Gly Ser Met Ile Gly Ser
    170       175       180

Phe Ile Asp Ile Tyr Gln Gln Glu Gly Thr Arg Gly Leu Trp Arg
    185       190       195

Gly Val Val Pro Thr Ala Gln Arg Ala Ala Ile Val Val Gly Val
    200       205       210

Glu Leu Pro Val Tyr Asp Ile Thr Lys Lys His Leu Ile Val Ser
    215       220       225

Gly Met Leu Gly Asp Thr Ile Leu Thr His Phe Val Ser Ser Phe
    230       235       240

Thr Cys Gly Leu Ala Gly Ala Leu Ala Ser Asn Pro Val Asp Val
    245       250       255

Val Arg Thr Arg Met Met Asn Gln Arg Ala Ile Val Gly His Val
    260       265       270

Asp Leu Tyr Lys Gly Thr Leu Asp Gly Ile Leu Lys Met Trp Lys
    275       280       285

His Glu Gly Phe Phe Ala Leu Tyr Lys Gly Phe Trp Pro Asn Trp
    290       295       300

Leu Arg Leu Gly Pro Trp Asn Ile Ile Phe Phe Ile Thr Tyr Glu
    305       310       315

Gln Leu Lys Arg Leu Gln Ile
    320       322

<210> SEQ ID NO 12
<211> LENGTH: 1031
<212> TYPE: DNA
<213> ORGANISM: Mus Musculus

<400> SEQUENCE: 12

| ctgcaggtcg actctagagg atccgaaatg gtatctttc ccggaataat | 50 |
|---|---|
| cctaattttt ctaagggtga agtttgcaac ggcggcagtg attgtaagcg | 100 |
| gacatcagaa aagttccact ttaagccatg agatgtctgg tctgaactgg | 150 |
| aaaccttttg tgtatggcgg ccttgcctct attgttgccg agttcggcac | 200 |
| tttccctgtg gatcttacta aaacacggct gcaagtccaa ggccagagta | 250 |
| tcgatgttcg tttcaaagaa ataaaatata gagggatgtt tcatgccttg | 300 |
| ttccgaatct ataagaaga agggatcttg ctctgtatt caggaattgc | 350 |
| ccctgcgtta ctaagacagg catcatatgg caccatcaaa attggtattt | 400 |
| atgaaagctt gaagcgatta tttgtagaac gtttggaaga tgagactctc | 450 |
| ctaattaaca tgatctgtgg ggtagtgtca ggagtgattt cctctactat | 500 |
| tgccaatccc actgatgttc taaagattcg aatgcaggct caaggaagtt | 550 |
| tgttccaagg gagcatgatt ggcagcttca ttgacatata ccagcaagaa | 600 |
| ggtaccaggg gtctgtggag gggtgtggtc ccaactgctc agcgtgctgc | 650 |
| aatcgttgtg ggagtagagc tgcccgttta tgatattacc aagaagcacc | 700 |
| tgatagtttc aggaatgctg ggagacacaa ttttaacaca ctttgtttcc | 750 |
| agtttcacct gtggtttggc tggggctctg gcatctaacc ctgtggatgt | 800 |
| ggtgagaact cgaatgatga atcagagggc aatagtggga catgtggacc | 850 |
| tctacaaggg tactttggat ggtattttaa agatgtggaa gcatgaggga | 900 |

```
tttttttgcac tctataaagg attttggcca aactggcttc gacttggacc         950
ctggaacatc atttttttta ttacctatga gcagctcaag aggcttcaga        1000
tctaagaatt caatcgatgg ccgccatggc c                            1031
```

<210> SEQ ID NO 13
<211> LENGTH: 325
<212> TYPE: PRT
<213> ORGANISM: Mus Musculus

<400> SEQUENCE: 13

```
Met Gly Ile Phe Pro Gly Ile Ile Leu Ile Phe Leu Arg Val Lys
 1               5                  10                  15

Phe Ala Thr Ala Ala Val Ile Val Ser Gly His Gln Lys Ser Ser
                20                  25                  30

Thr Leu Ser His Glu Met Ser Gly Leu Asn Trp Lys Pro Phe Val
                35                  40                  45

Tyr Gly Gly Leu Ala Ser Ile Val Ala Glu Phe Gly Thr Phe Pro
                50                  55                  60

Val Asp Leu Thr Lys Thr Arg Leu Gln Val Gln Gly Gln Ser Ile
                65                  70                  75

Asp Val Arg Phe Lys Glu Ile Lys Tyr Arg Gly Met Phe His Ala
                80                  85                  90

Leu Phe Arg Ile Tyr Lys Glu Glu Gly Ile Leu Ala Leu Tyr Ser
                95                 100                 105

Gly Ile Ala Pro Ala Leu Leu Arg Gln Ala Ser Tyr Gly Thr Ile
               110                 115                 120

Lys Ile Gly Ile Tyr Gln Ser Leu Lys Arg Leu Phe Val Glu Arg
               125                 130                 135

Leu Glu Asp Glu Thr Leu Leu Ile Asn Met Ile Cys Gly Val Val
               140                 145                 150

Ser Gly Val Ile Ser Ser Thr Ile Ala Asn Pro Thr Asp Val Leu
               155                 160                 165

Lys Ile Arg Met Gln Ala Gln Gly Ser Leu Phe Gln Gly Ser Met
               170                 175                 180

Ile Gly Ser Phe Ile Asp Ile Tyr Gln Gln Glu Gly Thr Arg Gly
               185                 190                 195

Leu Trp Arg Gly Val Val Pro Thr Ala Gln Arg Ala Ala Ile Val
               200                 205                 210

Val Gly Val Glu Leu Pro Val Tyr Asp Ile Thr Lys Lys His Leu
               215                 220                 225

Ile Val Ser Gly Met Leu Gly Asp Thr Ile Leu Thr His Phe Val
               230                 235                 240

Ser Ser Phe Thr Cys Gly Leu Ala Gly Ala Leu Ala Ser Asn Pro
               245                 250                 255

Val Asp Val Val Arg Thr Arg Met Met Asn Gln Arg Ala Ile Val
               260                 265                 270

Gly His Val Asp Leu Tyr Lys Gly Thr Leu Asp Gly Ile Leu Lys
               275                 280                 285

Met Trp Lys His Glu Gly Phe Phe Ala Leu Tyr Lys Gly Phe Trp
               290                 295                 300

Pro Asn Trp Leu Arg Leu Gly Pro Trp Asn Ile Ile Phe Phe Ile
               305                 310                 315

Thr Tyr Glu Gln Leu Lys Arg Leu Gln Ile
               320                 325
```

<210> SEQ ID NO 14
<211> LENGTH: 17
<212> TYPE: DNA
<213> ORGANISM: Artificial
<220> FEATURE:
<221> NAME/KEY: Misc_feature
<222> LOCATION: 1-17
<223> OTHER INFORMATION: sequence is synthesized

<400> SEQUENCE: 14
aaatttgcaa cggcggc                                                  17

<210> SEQ ID NO 15
<211> LENGTH: 22
<212> TYPE: DNA
<213> ORGANISM: Artificial
<220> FEATURE:
<221> NAME/KEY: Misc_feature
<222> LOCATION: 1-22
<223> OTHER INFORMATION: sequence is synthesized

<400> SEQUENCE: 15
tcagaccaga catttcatgg ct                                            22

<210> SEQ ID NO 16
<211> LENGTH: 34
<212> TYPE: DNA
<213> ORGANISM: Artificial
<220> FEATURE:
<221> NAME/KEY: Misc_feature
<222> LOCATION: 1-34
<223> OTHER INFORMATION: sequence is synthesized

<400> SEQUENCE: 16
tgattgtaag cggacatcag aaaagttcca cttt                               34

<210> SEQ ID NO 17
<211> LENGTH: 19
<212> TYPE: DNA
<213> ORGANISM: Artificial
<220> FEATURE:
<221> NAME/KEY: Misc_feature
<222> LOCATION: 1-19
<223> OTHER INFORMATION: sequence is synthesized

<400> SEQUENCE: 17
gggtgtggtc ccaactgct                                                19

<210> SEQ ID NO 18
<211> LENGTH: 25
<212> TYPE: DNA
<213> ORGANISM: Artificial
<220> FEATURE:
<221> NAME/KEY: Misc_feature
<222> LOCATION: 1-25
<223> OTHER INFORMATION: sequence is synthesized

<400> SEQUENCE: 18
ttcttggtaa tatcataaac gggca                                         25

<210> SEQ ID NO 19
<211> LENGTH: 27
<212> TYPE: DNA
<213> ORGANISM: Artificial
<220> FEATURE:
<221> NAME/KEY: Misc_feature
<222> LOCATION: 1-27

<223> OTHER INFORMATION: sequence is synthesized

<400> SEQUENCE: 19
cgtgctgcaa tcgttgtggg agtagag                27

<210> SEQ ID NO 20
<211> LENGTH: 24
<212> TYPE: DNA
<213> ORGANISM: Artificial
<220> FEATURE:
<221> NAME/KEY: Misc_feature
<222> LOCATION: 1-24
<223> OTHER INFORMATION: sequence is synthesized

<400> SEQUENCE: 20
gaaatcgtgc gtgacatcaa agag                24

<210> SEQ ID NO 21
<211> LENGTH: 23
<212> TYPE: DNA
<213> ORGANISM: Artificial
<220> FEATURE:
<221> NAME/KEY: Misc_feature
<222> LOCATION: 1-23
<223> OTHER INFORMATION: sequence is synthesized

<400> SEQUENCE: 21
ctccttctgc atcctgtcag caa                23

<210> SEQ ID NO 22
<211> LENGTH: 22
<212> TYPE: DNA
<213> ORGANISM: Artificial
<220> FEATURE:
<221> NAME/KEY: Misc_feature
<222> LOCATION: 1-22
<223> OTHER INFORMATION: sequence is synthesized

<400> SEQUENCE: 22
cggttccgat gccctgaggc tc                22

<210> SEQ ID NO 23
<211> LENGTH: 28
<212> TYPE: DNA
<213> ORGANISM: Artificial
<220> FEATURE:
<221> NAME/KEY: Misc_feature
<222> LOCATION: 1-28
<223> OTHER INFORMATION: sequence is synthesized

<400> SEQUENCE: 23
ggaataatcc taaattttct aagggtga                28

<210> SEQ ID NO 24
<211> LENGTH: 22
<212> TYPE: DNA
<213> ORGANISM: Artificial
<220> FEATURE:
<221> NAME/KEY: Misc_feature
<222> LOCATION: 1-22
<223> OTHER INFORMATION: sequence is synthesized

<400> SEQUENCE: 24
cttttctggt gtccgcttac aa                22

<210> SEQ ID NO 25
<211> LENGTH: 18

```
<212> TYPE: DNA
<213> ORGANISM: Artificial
<220> FEATURE:
<221> NAME/KEY: Misc_feature
<222> LOCATION: 1-18
<223> OTHER INFORMATION: sequence is synthesized

<400> SEQUENCE: 25
tttgcaacgg cggccgtg                                              18

<210> SEQ ID NO 26
<211> LENGTH: 21
<212> TYPE: DNA
<213> ORGANISM: Artificial
<220> FEATURE:
<221> NAME/KEY: Misc_feature
<222> LOCATION: 1-21
<223> OTHER INFORMATION: sequence is synthesized

<400> SEQUENCE: 26
ggctctgtgg aggtgcttat g                                          21

<210> SEQ ID NO 27
<211> LENGTH: 20
<212> TYPE: DNA
<213> ORGANISM: Artificial
<220> FEATURE:
<221> NAME/KEY: Misc_feature
<222> LOCATION: 1-20
<223> OTHER INFORMATION: sequence is synthesized

<400> SEQUENCE: 27
tgggattaca ggcatgagcc                                            20

<210> SEQ ID NO 28
<211> LENGTH: 26
<212> TYPE: DNA
<213> ORGANISM: Artificial
<220> FEATURE:
<221> NAME/KEY: Misc_feature
<222> LOCATION: 1-26
<223> OTHER INFORMATION: sequence is synthesized

<400> SEQUENCE: 28
caaaagctgt taccggctgt gtgctg                                     26

<210> SEQ ID NO 29
<211> LENGTH: 19
<212> TYPE: DNA
<213> ORGANISM: Artificial
<220> FEATURE:
<221> NAME/KEY: Misc_feature
<222> LOCATION: 1-19
<223> OTHER INFORMATION: sequence is synthesized

<400> SEQUENCE: 29
ggatgttcca tgcgctgtt                                             19

<210> SEQ ID NO 30
<211> LENGTH: 19
<212> TYPE: DNA
<213> ORGANISM: Artificial
<220> FEATURE:
<221> NAME/KEY: Misc_feature
<222> LOCATION: 1-19
<223> OTHER INFORMATION: sequence is synthesized

<400> SEQUENCE: 30
```

-continued

| cgcaggagca attcctgaa | 19 |

<210> SEQ ID NO 31
<211> LENGTH: 33
<212> TYPE: DNA
<213> ORGANISM: Artificial
<220> FEATURE:
<221> NAME/KEY: Misc_feature
<222> LOCATION: 1-33
<223> OTHER INFORMATION: sequence is synthesized

<400> SEQUENCE: 31

| cgcatctgta aagaggaagg tgtattggct ctc | 33 |

<210> SEQ ID NO 32
<211> LENGTH: 993
<212> TYPE: DNA
<213> ORGANISM: Homo Sapien

<400> SEQUENCE: 32

| gaattcttag atttgaagcc tctttagctg ctcgtatgta ataaaaaaaa | 50 |
| tgatgttcca gggtccaagc cgaagccagt ttggccaaaa tcctttatag | 100 |
| agtgcaaaaa agccctcatg tttccacatc tttaaaatac catcaacagt | 150 |
| gcccttatag agatccacat gtcccacgat tgccctctgg ttcatcatgc | 200 |
| gagttcgaac cacatcaacc gggttggagg ccagagcccc agccaaacca | 250 |
| catgtaaagc tggaaacgaa gtgagttaaa attgtatcgc ccatcattcc | 300 |
| tgacaatatt aaatgcttct tagtaatatc atagactggt agctctactc | 350 |
| ctacaacgat ggcagcacgc tgagcagttg aaccacacc cctccacaga | 400 |
| cccctggtgc cttcttgttg gtatatatcg ataaagcttc caatcatgct | 450 |
| cccttggaac aagcttcctt gagcctgcat tcgaatcttt agaacatcgg | 500 |
| tgggattggc tatagtggaa gatatcactc ctgacactac cccacagatc | 550 |
| atattaatta aaagagtttc atcttctaaa cgttctacga ataagcgctt | 600 |
| caagctttgg taaatcccaa ttttaatggt gccatatgat gcttgtctta | 650 |
| gcaacgcagg agcaattcct gaatagagag ccaatacacc ttcctctttta | 700 |
| cagatgcgaa acagcgcatg gaacatccct ctatatttta tctctttgaa | 750 |
| acgggcatca atgctttggc cttgaacctg aagtcgtgtt ttggtaaggt | 800 |
| ccacagggaa agtcccaaac tcagccacga tagaggcaag gccgccatat | 850 |
| acaaagggtt tccaattcag accagacatc tcatgactta cagtggtact | 900 |
| tttctggtgt ccgcttacaa tcacggccgc cgttgcaaac ttcacccta | 950 |
| gaaaaattag gattattccg ggaaagatac ccatggcgga tcc | 993 |

<210> SEQ ID NO 33
<211> LENGTH: 307
<212> TYPE: PRT
<213> ORGANISM: Homo Sapien

<400> SEQUENCE: 33

Met Gly Gly Leu Thr Ala Ser Asp Val His Pro Thr Leu Gly Val
 1               5                  10                  15

Gln Leu Phe Ser Ala Pro Ile Ala Ala Cys Leu Ala Asp Val Ile
                20                  25                  30

Thr Phe Pro Leu Asp Thr Ala Lys Val Arg Leu Gln Val Gln Gly

-continued

```
                      35                  40                  45
Glu Cys Pro Thr Ser Ser Val Ile Arg Tyr Lys Gly Val Leu Gly
             50                  55                  60
Thr Ile Thr Ala Val Val Lys Thr Gly Arg Met Lys Leu Tyr
         65                  70                  75
Ser Gly Leu Pro Ala Gly Leu Gln Arg Gln Ile Ser Ser Ala Ser
                 80                  85                  90
Leu Arg Ile Gly Leu Tyr Asp Thr Val Gln Glu Phe Leu Thr Ala
                 95                 100                 105
Gly Lys Glu Thr Ala Pro Ser Leu Gly Ser Lys Ile Leu Ala Gly
                110                 115                 120
Leu Thr Thr Gly Gly Val Ala Val Phe Ile Gly Gln Pro Thr Glu
                125                 130                 135
Val Val Lys Val Arg Leu Gln Ala Gln Ser His Leu His Gly Ile
                140                 145                 150
Lys Pro Arg Tyr Thr Gly Thr Tyr Asn Ala Tyr Arg Ile Ile Ala
                155                 160                 165
Thr Thr Glu Gly Leu Thr Gly Leu Trp Lys Gly Thr Thr Pro Asn
                170                 175                 180
Leu Met Arg Ser Val Ile Ile Asn Cys Thr Glu Leu Val Thr Tyr
                185                 190                 195
Asp Leu Met Lys Glu Ala Phe Val Lys Asn Asn Ile Leu Ala Asp
                200                 205                 210
Asp Val Pro Cys His Leu Val Ser Ala Leu Ile Ala Gly Phe Cys
                215                 220                 225
Ala Thr Ala Met Ser Ser Pro Val Asp Val Val Lys Thr Arg Phe
                230                 235                 240
Ile Asn Ser Pro Pro Gly Gln Tyr Lys Ser Val Pro Asn Cys Ala
                245                 250                 255
Met Lys Val Phe Thr Asn Glu Gly Pro Thr Ala Phe Phe Lys Gly
                260                 265                 270
Leu Val Pro Ser Phe Leu Arg Leu Gly Ser Trp Asn Val Ile Met
                275                 280                 285
Phe Val Cys Phe Glu Gln Leu Lys Arg Glu Leu Ser Lys Ser Arg
                290                 295                 300
Gln Thr Met Asp Cys Ala Thr
                305     307
```

<210> SEQ ID NO 34
<211> LENGTH: 309
<212> TYPE: PRT
<213> ORGANISM: Homo Sapien

<400> SEQUENCE: 34

```
Met Val Gly Phe Lys Ala Thr Asp Val Pro Pro Thr Ala Thr Val
 1               5                  10                  15
Lys Phe Leu Gly Ala Gly Thr Ala Ala Cys Ile Ala Asp Leu Ile
                20                  25                  30
Thr Phe Pro Leu Asp Thr Ala Lys Val Arg Leu Gln Ile Gln Gly
                35                  40                  45
Glu Ser Gln Gly Pro Val Arg Ala Thr Ala Ser Ala Gln Tyr Arg
                50                  55                  60
Gly Val Met Gly Thr Ile Leu Thr Met Val Arg Thr Glu Gly Pro
                65                  70                  75
```

-continued

```
Arg Ser Leu Tyr Asn Gly Leu Val Ala Gly Leu Gln Arg Gln Met
             80                  85                  90

Ser Phe Ala Ser Val Arg Ile Gly Leu Tyr Asp Ser Val Lys Gln
             95                 100                 105

Phe Tyr Thr Lys Gly Ser Glu His Ala Ser Ile Gly Ser Arg Leu
            110                 115                 120

Leu Ala Gly Ser Thr Thr Gly Ala Leu Ala Val Ala Val Ala Gln
            125                 130                 135

Pro Thr Asp Val Val Lys Val Arg Phe Gln Ala Gln Ala Arg Ala
            140                 145                 150

Gly Gly Gly Arg Arg Tyr Gln Ser Thr Val Asn Ala Tyr Lys Thr
            155                 160                 165

Ile Ala Arg Glu Glu Gly Phe Arg Gly Leu Trp Lys Gly Thr Ser
            170                 175                 180

Pro Asn Val Ala Arg Asn Ala Ile Val Asn Cys Ala Glu Leu Val
            185                 190                 195

Thr Tyr Asp Leu Ile Lys Asp Ala Leu Leu Lys Ala Asn Leu Met
            200                 205                 210

Thr Asp Asp Leu Pro Cys His Phe Thr Ser Ala Phe Gly Ala Gly
            215                 220                 225

Phe Cys Thr Thr Val Ile Ala Ser Pro Val Asp Val Val Lys Thr
            230                 235                 240

Arg Tyr Met Asn Ser Ala Leu Gly Gln Tyr Ser Ser Ala Gly His
            245                 250                 255

Cys Ala Leu Thr Met Leu Gln Lys Glu Gly Pro Arg Ala Phe Tyr
            260                 265                 270

Lys Gly Phe Met Pro Ser Phe Leu Arg Leu Gly Ser Trp Asn Val
            275                 280                 285

Val Met Phe Val Thr Tyr Glu Gln Leu Lys Arg Ala Leu Met Ala
            290                 295                 300

Ala Cys Thr Ser Arg Glu Ala Pro Phe
            305                 309

<210> SEQ ID NO 35
<211> LENGTH: 300
<212> TYPE: PRT
<213> ORGANISM: Homo Sapien

<400> SEQUENCE: 35

Met Ala Val Lys Phe Leu Gly Ala Gly Thr Ala Ala Cys Phe Ala
  1               5                  10                  15

Asp Leu Val Thr Phe Pro Leu Asp Thr Ala Lys Val Arg Leu Gln
             20                  25                  30

Ile Gln Gly Glu Asn Gln Ala Val Gln Thr Ala Arg Leu Val Gln
             35                  40                  45

Tyr Arg Gly Val Leu Gly Thr Ile Leu Thr Met Val Arg Thr Glu
             50                  55                  60

Gly Pro Cys Ser Pro Tyr Asn Gly Leu Val Ala Gly Leu Gln Arg
             65                  70                  75

Gln Met Ser Phe Ala Ser Ile Arg Ile Gly Leu Tyr Asp Ser Val
             80                  85                  90

Lys Gln Val Tyr Thr Pro Lys Gly Ala Asp Asn Ser Ser Leu Thr
             95                 100                 105

Thr Arg Ile Leu Ala Gly Cys Thr Thr Gly Ala Met Ala Val Thr
            110                 115                 120
```

-continued

Cys Ala Gln Pro Thr Asp Val Val Lys Val Arg Phe Gln Ala Ser
                125                 130                 135

Ile His Leu Gly Pro Ser Arg Ser Asp Arg Lys Tyr Ser Gly Thr
                140                 145                 150

Met Asp Ala Tyr Arg Thr Ile Ala Arg Glu Glu Gly Val Arg Gly
                155                 160                 165

Leu Trp Lys Gly Thr Leu Pro Asn Ile Met Arg Asn Ala Ile Val
                170                 175                 180

Asn Cys Ala Glu Val Val Thr Tyr Asp Ile Leu Lys Glu Lys Leu
                185                 190                 195

Leu Asp Tyr His Leu Leu Thr Asp Asn Phe Pro Cys His Phe Val
                200                 205                 210

Ser Ala Phe Gly Ala Gly Phe Cys Ala Thr Val Val Ala Ser Pro
                215                 220                 225

Val Asp Val Val Lys Thr Arg Tyr Met Asn Ser Pro Pro Gly Gln
                230                 235                 240

Tyr Phe Ser Pro Leu Asp Cys Met Ile Lys Met Val Ala Gln Glu
                245                 250                 255

Gly Pro Thr Ala Phe Tyr Lys Gly Phe Thr Pro Ser Phe Leu Arg
                260                 265                 270

Leu Gly Ser Trp Asn Val Val Met Phe Val Thr Tyr Glu Gln Leu
                275                 280                 285

Lys Arg Ala Leu Met Lys Val Gln Met Leu Arg Glu Ser Pro Phe
                290                 295                 300

<210> SEQ ID NO 36
<211> LENGTH: 323
<212> TYPE: PRT
<213> ORGANISM: Homo Sapien

<400> SEQUENCE: 36

Met Ser Val Pro Glu Glu Glu Arg Leu Leu Pro Leu Thr Gln
 1               5                  10                  15

Arg Trp Pro Arg Ala Ser Lys Phe Leu Leu Ser Gly Cys Ala Ala
                20                  25                  30

Thr Val Ala Glu Leu Ala Thr Phe Pro Leu Asp Leu Thr Lys Thr
                35                  40                  45

Arg Leu Gln Met Gln Gly Glu Ala Ala Leu Ala Arg Leu Gly Asp
                50                  55                  60

Gly Ala Arg Glu Ser Ala Pro Tyr Arg Gly Met Val Arg Thr Ala
                65                  70                  75

Leu Gly Ile Ile Glu Glu Glu Gly Phe Leu Lys Leu Trp Gln Gly
                80                  85                  90

Val Thr Pro Ala Ile Tyr Arg His Val Val Tyr Ser Gly Gly Arg
                95                  100                 105

Met Val Thr Tyr Glu His Leu Arg Glu Val Phe Gly Lys Ser
                110                 115                 120

Glu Asp Glu His Tyr Pro Leu Trp Lys Ser Val Ile Gly Gly Met
                125                 130                 135

Met Ala Gly Val Ile Gly Gln Phe Leu Ala Asn Pro Thr Asp Leu
                140                 145                 150

Val Lys Val Gln Met Gln Met Glu Gly Lys Arg Lys Leu Glu Gly
                155                 160                 165

Lys Pro Leu Arg Phe Arg Gly Val His His Ala Phe Ala Lys Ile

-continued

```
                    170                 175                 180
Leu Ala Glu Gly Gly Ile Arg Gly Leu Trp Ala Gly Trp Val Pro
                185                 190                 195

Asn Ile Gln Arg Ala Ala Leu Val Asn Met Gly Asp Leu Thr Thr
                200                 205                 210

Tyr Asp Thr Val Lys His Tyr Leu Val Leu Asn Thr Pro Leu Glu
                215                 220                 225

Asp Asn Ile Met Thr His Gly Leu Ser Ser Leu Cys Ser Gly Leu
                230                 235                 240

Val Ala Ser Ile Leu Gly Thr Pro Ala Asp Val Ile Lys Ser Arg
                245                 250                 255

Ile Met Asn Gln Pro Arg Asp Lys Gln Gly Arg Gly Leu Leu Tyr
                260                 265                 270

Lys Ser Ser Thr Asp Cys Leu Ile Gln Ala Val Gln Gly Glu Gly
                275                 280                 285

Phe Met Ser Leu Tyr Lys Gly Phe Leu Pro Ser Trp Leu Arg Met
                290                 295                 300

Thr Pro Trp Ser Met Val Phe Trp Leu Thr Tyr Glu Lys Ile Arg
                305                 310                 315

Glu Met Ser Gly Val Ser Pro Phe
                320         323
```